United States Patent
Cohen et al.

(10) Patent No.: US 9,155,775 B1
(45) Date of Patent: Oct. 13, 2015

(54) PROCESS FOR MANUFACTURING GLATIRAMER ACETATE PRODUCT

(71) Applicants: Rakefet Cohen, Kokhav Ya'ir-Tzur Yigal (IL); Sasson Habbah, Kokhav Ya'ir-Tzur Yigal (IL); Muhammad Safadi, Nazareth (IL)

(72) Inventors: Rakefet Cohen, Kokhav Ya'ir-Tzur Yigal (IL); Sasson Habbah, Kokhav Ya'ir-Tzur Yigal (IL); Muhammad Safadi, Nazareth (IL)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 0 days.

(21) Appl. No.: 14/608,126

(22) Filed: Jan. 28, 2015

(51) Int. Cl.
*A61K 38/02* (2006.01)

(52) U.S. Cl.
CPC ..................... *A61K 38/02* (2013.01)

(58) Field of Classification Search
CPC ....................................................... A61K 38/02
See application file for complete search history.

(56) References Cited

U.S. PATENT DOCUMENTS

| | | | |
|---|---|---|---|
| 3,849,550 A | 11/1974 | Teitelbaum et al. |
| 5,800,808 A | 9/1998 | Konfino et al. |
| 5,981,589 A | 11/1999 | Konfino et al. |
| 6,048,898 A | 4/2000 | Konfino et al. |
| 6,054,430 A | 4/2000 | Konfino et al. |
| 6,214,791 B1 | 4/2001 | Arnon et al. |
| 6,342,476 B1 | 1/2002 | Konfino et al. |
| 6,362,161 B1 | 3/2002 | Konfino et al. |
| 6,514,938 B1 | 2/2003 | Gad et al. |
| 6,620,847 B2 | 9/2003 | Konfino et al. |
| 6,800,285 B2 | 10/2004 | Rodriguez et al. |
| 6,800,287 B2 | 10/2004 | Gad et al. |
| 6,939,539 B2 | 9/2005 | Konfino et al. |
| 7,022,663 B2 | 4/2006 | Gilbert et al. |
| 7,033,582 B2 | 4/2006 | Yong et al. |
| 7,049,399 B2 | 5/2006 | Bejan et al. |
| 7,074,580 B2 | 7/2006 | Gad et al. |
| 7,163,802 B2 | 1/2007 | Gad et al. |
| 7,199,098 B2 | 4/2007 | Konfino et al. |
| 7,279,172 B2 | 10/2007 | Aharoni et al. |
| 7,425,332 B2 | 9/2008 | Aharoni et al. |
| 7,429,374 B2 | 9/2008 | Klinger |
| 7,495,072 B2 | 2/2009 | Dolitzky |
| 7,560,100 B2 | 7/2009 | Pinchasi et al. |
| 7,566,767 B2 | 7/2009 | Strominger et al. |
| 7,615,359 B2 | 11/2009 | Gad et al. |
| 7,625,861 B2 | 12/2009 | Konfino et al. |
| 7,855,176 B1 | 12/2010 | Altman et al. |
| 7,923,215 B2 | 4/2011 | Klinger |
| 7,968,511 B2 | 6/2011 | Vollmer et al. |
| 8,008,258 B2 | 8/2011 | Aharoni et al. |
| 8,232,250 B2 | 7/2012 | Klinger |
| 8,367,605 B2 | 2/2013 | Konfino et al. |
| 8,389,228 B2 | 3/2013 | Klinger |
| 8,399,211 B2 | 3/2013 | Gad et al. |
| 8,399,413 B2 | 3/2013 | Klinger |
| 8,536,305 B2 | 9/2013 | Ray et al. |
| 8,709,433 B2 | 4/2014 | Kasper |
| 8,729,229 B2 | 5/2014 | Ray et al. |
| 8,759,302 B2 | 6/2014 | Dhib-Jalbut |
| 8,815,511 B2 | 8/2014 | Tchelet et al. |
| 8,920,373 B2 | 12/2014 | Altman et al. |
| 8,969,302 B2 | 3/2015 | Klinger |
| 2002/0077278 A1 | 6/2002 | Yong et al. |
| 2005/0019322 A1 | 1/2005 | Rodriguez et al. |
| 2005/0170004 A1 | 8/2005 | Rosenberger |
| 2006/0172942 A1 | 8/2006 | Dolitzky |
| 2006/0189527 A1 | 8/2006 | Rasmussen et al. |
| 2006/0194725 A1 | 8/2006 | Rasmussen et al. |
| 2006/0240463 A1 | 10/2006 | Lancet |
| 2006/0264354 A1 | 11/2006 | Aharoni et al. |
| 2007/0021324 A1 | 1/2007 | Dolitzky |
| 2007/0037740 A1 | 2/2007 | Pinchasi et al. |
| 2007/0054857 A1 | 3/2007 | Pinchasi et al. |

(Continued)

FOREIGN PATENT DOCUMENTS

| WO | WO 98/30227 | 7/1998 |
|---|---|---|
| WO | WO 00/18794 | 9/1999 |

(Continued)

OTHER PUBLICATIONS

The Copaxone Prescribing Label, 2009—better copy.*

(Continued)

*Primary Examiner* — Sue Liu
*Assistant Examiner* — Thor Nielsen
(74) *Attorney, Agent, or Firm* — John P. White; Gary J. Gershik; Cooper & Dunham LLP

(57) ABSTRACT

The patent provides a process of preparing a pharmaceutical preparation of glatiramer acetate and mannitol in a suitable container comprising the steps of:

(i) obtaining an aqueous pharmaceutical solution of glatiramer acetate and mannitol;

(ii) filtering the aqueous pharmaceutical solution at a temperature of from above 0° C. up to 17.5° C. to produce a filtrate; and (iii) filling the suitable container with the filtrate obtained after performing step (ii), so as to thereby prepare the pharmaceutical preparation of glatiramer acetate and mannitol in the suitable container.

This patent further provides an aqueous pharmaceutical solution comprising 40 mg/ml glatiramer acetate and 40 mg/ml mannitol, wherein the aqueous pharmaceutical solution a) has a viscosity in the range of 2.0-3.5 cPa; or b) has an osmolality in the range of 275-325 mosmol/Kg.

This patent also provides a prefilled syringe, an automated injector and a method of treatment of a human patient.

27 Claims, 11 Drawing Sheets

(56) References Cited

U.S. PATENT DOCUMENTS

| | | | |
|---|---|---|---|
| 2007/0059798 | A1 | 3/2007 | Gad |
| 2007/0161566 | A1* | 7/2007 | Pinchasi .................... 514/12 |
| 2007/0244056 | A1 | 10/2007 | Hayardeny et al. |
| 2008/0021192 | A1 | 1/2008 | Iyer et al. |
| 2008/0118553 | A1 | 5/2008 | Frenkel et al. |
| 2008/0207526 | A1 | 8/2008 | Strominger |
| 2008/0261894 | A1 | 10/2008 | Kreitman et al. |
| 2009/0048181 | A1 | 2/2009 | Schipper et al. |
| 2009/0149541 | A1 | 6/2009 | Stark et al. |
| 2010/0167983 | A1 | 7/2010 | Kreitman et al. |
| 2010/0285600 | A1 | 11/2010 | Lancet et al. |
| 2010/0298227 | A1 | 11/2010 | Aharoni et al. |
| 2010/0305023 | A1 | 12/2010 | Stark et al. |
| 2010/0324265 | A1 | 12/2010 | Kota et al. |
| 2011/0060279 | A1 | 3/2011 | Altman et al. |
| 2011/0066112 | A1 | 3/2011 | Altman et al. |
| 2012/0027718 | A1 | 2/2012 | Kreitman et al. |
| 2012/0309671 | A1 | 12/2012 | Klinger |
| 2013/0165387 | A1 | 6/2013 | Klinger |
| 2013/0323771 | A1 | 12/2013 | Sathe et al. |
| 2014/0107208 | A1 | 4/2014 | Comabella et al. |
| 2014/0193827 | A1 | 7/2014 | Schwartz et al. |
| 2014/0271532 | A1 | 9/2014 | Kreitman et al. |
| 2014/0271630 | A1 | 9/2014 | Vollmer |
| 2014/0294899 | A1 | 10/2014 | Kasper et al. |
| 2014/0322158 | A1 | 10/2014 | Dhib-Jalbut |
| 2015/0045306 | A1 | 2/2015 | Tchelet et al. |
| 2015/0110733 | A1 | 4/2015 | Tchelet et al. |

FOREIGN PATENT DOCUMENTS

| | | |
|---|---|---|
| WO | WO 00/05250 | 2/2000 |
| WO | WO 00/05249 | 3/2000 |
| WO | WO 00/20010 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2005/041933 | 6/2003 |
| WO | WO 2004/103297 | 2/2004 |
| WO | WO 2004/064717 | 8/2004 |
| WO | WO 2004/091573 | 10/2004 |
| WO | WO 2006/029036 | 3/2006 |
| WO | WO 2006/029393 | 3/2006 |
| WO | WO 2006/029411 | 3/2006 |
| WO | WO 2006/083608 | 8/2006 |
| WO | WO 2006/089164 | 8/2006 |
| WO | WO 2006/116602 | 11/2006 |
| WO | WO 2007/030573 | 3/2007 |
| WO | WO 2007/081975 | 7/2007 |
| WO | WO 2008157697 | 12/2008 |
| WO | WO 2009/070298 | 6/2009 |
| WO | WO 2011/022063 | 8/2010 |
| WO | WO 2011/008274 | 1/2011 |
| WO | WO 2012/051106 | 4/2012 |
| WO | WO 2013/055683 | 4/2013 |
| WO | WO 2014/058976 | 4/2014 |
| WO | WO 2014/107533 | 7/2014 |
| WO | WO 2014128079 | 8/2014 |
| WO | WO 2014/165280 | 10/2014 |
| WO | WO 2015-061367 | 4/2015 |

OTHER PUBLICATIONS

Sondhi et al., Ceramic membranes: Applications & Benefits—from "A" to "Z", Fluid/Particle Separation Journal 14: 130-134 (2002).*
Feb. 6, 2015 Petition for Inter Partes Review, filed in connection with *Mylan Pharmaceuticals Inc.* v. *Yeda Research & Development Co. Ltd.* For U.S. Pat. No. 8,232,250 in the United States Patent and Trademark Office Patent Trial and Appeal Board (Case No. IPR2015-00643).
Declaration of Stephen J. Peroutka, M.D., Ph.D., cited in Feb. 6, 2015 Petition for Inter Partes Review (Case No. IPR2015-00643).
Expert Declaration of Ari Green, M.D. in Support of Petition for Inter Partes Review of U.S. Pat. No. 8,232,250, cited in Feb. 6, 2015 Petition for Inter Partes Review (Case No. IPR2015-00643).
Feb. 7, 2015 Petition for Inter Partes Review filed in connection with *Mylan Pharmaceuticals Inc.* v. *Yeda Research & Development Co. Ltd.* For U.S. Pat. No. 8,399,413 in the United States Patent and Trademark Office Patent Trial and Appeal Board (Case No. IPR2015-00644).
Declaration of Stephen J. Peroutka, M.D., Ph.D., cited in Feb. 7, 2015 Petition for Inter Partes Review (Case No. IPR2015-00644).
Expert Declaration of Ari Green, M.D. in Support of Petition for Inter Partes Review of U.S. Pat. No. 8,232,250, cited in Feb. 7, 2015 Petition for Inter Partes Review (Case No. IPR2015-00644).
PCT International Application Publication No. WO 2007/081975, published Jul. 19, 2007 (Pinchasi), cited in Feb. 6, 2015 Petition for Inter Partes Review (Case No. IPR2015-00643) and Feb. 7, 2015 Petition for Inter Partes Review (Case No. IPR2015-00644).
Cohen et al., "Randomized, double-blind, dose comparison study of glatiramer acetate in relapsing-remitting MS". Neurology, 2007, 68: 939-944, cited in Feb. 6, 2015 Petition for Inter Partes Review (Case No. IPR2015-00643) and Feb. 7, 2015 Petition for Inter Partes Review (Case No. IPR2015-00644).
Flechter S, et al., "Copolymer 1 (Glatiramer Acetate) in Relapsing Forms of Multiple Sclerosis: Open Multicenter Study of Alternate-Day Administration" Clinical Neuropharmacology, 2002, 25: 11-15, cited in Feb. 6, 2015 Petition for Inter Partes Review (Case No. 1PR2015-00643) and Feb. 7, 2015 Petition for Inter Partes Review (Case No. IPR2015-00644).
Khan et al., "Randomized, prospective, rater-blinded, four-year, pilot study to compare the effect of daily versus every-other-day injections in relapsing-remitting multiple sclerosis" Mult. Scler. 2008, 14 Suppl. 1 S296, cited in Feb. 6, 2015 Petition for Inter Partes Review (Case No. IPR2015-00643) and Feb. 7, 2015 Petition for Inter Partes Review (Case No. IPR2015-00644).
Caon et al., "Randomized, prospective, rater-blinded, four year pilot study to compare the effect of daily versus every other day glatiramer acetate 20 mg subcutaneous injections in RRMS" Neurology, 2009, vol. 72, No. 11, p. A317, cited in Feb. 6, 2015 Petition for Inter Partes Review (Case No. IPR2015-00643) and Feb. 7, 2015 Petition for Inter Partes Review (Case No. IPR2015-00644).
Teva Provides Update on Forte Trial Jerusalem, Israel (Jul. 7, 2008), cited in Feb. 7, 2015 Petition for Inter Partes Review (Case No. IPR2015-00644).
Frohman et al., "Multiple Sclerosis—The Plaque and its Pathogenesis" New England J. Med. 2006, 354:942-55, cited in Feb. 7, 2015 Petition for Inter Partes Review (Case No. IPR2015-00644).
Copaxone®, Food and Drug Administration Approved Labeling, 2001 (NDA 20-622/S-015/S-015) cited in Feb. 7, 2015 Petition for Inter Partes Review (Case No. IPR2015-00644).
Copaxone®, Food and Drug Administration Approved Labeling, Feb. 2009, cited in Feb. 7, 2015 Petition for Inter Partes Review (Case No. IPR2015-00644).
Jacobs et al., "Intramuscular interferon beta-la therapy initiated during a first demyelinating event in multiple sclerosis" New Engl. J. Med. 2000, 343:898-904, cited in Feb. 7, 2015 Petition for Inter Partes Review (Case No. IPR2015-00644).
U.S. Appl. No. 11/258,850, filed Sep. 14, 2005 (Schwartz et al.). The specification and claims as originally filed.
U.S. Appl. No. 11/654,374, filed Jan. 16, 2007 (Schwartz et al.). The specification and claims as originally filed.
U.S. Appl. No. 14/520,280, filed Oct. 21, 2014 (Tchelet et al.). The specification and claims as originally filed.
Citizen Petition Requesting That FDA Refrain From Approving Any Abbreviated New Drug Application Referencing Copaxone® (glatiramer acetate injection) Until Certain Conditions Are Met, Jul. 2, 2014 [online]. Regulations.gov [retrieved on Feb. 19, 2015]. Retrieved from the Internet: <URL: www.regulations.gov/#!documentDetail;D=FDA-2014-P-0933-0001>.
Citizen Petition Requesting That FDA Refrain From Approving Any Abbreviated New Drug Application Referencing Copaxone® (Glatiramer Acetate Injection) Until Certain Conditions Are Met, Dec. 5, 2013 [online]. Regulations.gov [retrieved on Feb. 19, 2015].

(56) References Cited

OTHER PUBLICATIONS

Retrieved from the Internet: <URL: www.regulations.gov/#!documentDetail;D=FDA-2013-P-1641-0001>.
Sep. 10, 2014 Complaint, filed in connection with *Teva Pharmaceuticals USA, Inc.*, et al., v. *Sandoz Inc.* and Momenta Pharmaceuticals, Inc. in the the United States District Court for District of Delaware (Case No. 1:14-cv-001171-GMS).
Nov. 3, 2014 Answer, filed in connection with *Teva Pharmaceuticals USA, Inc., et al.*, v. *Sandoz Inc.* and Momenta Pharmaceuticals, Inc. in the United States District Court for the District of Delaware (Case No. 1:14-cv-001171-GMS).
Dec. 1, 2014 Answer to Counterclaims, filed in connection with *Teva Pharmaceuticals USA, Inc., et al.*, v. *Sandoz Inc.* and Momenta Pharmaceuticals, Inc. in the United States District Court for District of Delaware (Case No. 1:14-cv-001171-GMS).
Sep. 10, 2014 Complaint, filed in connection with *Teva Pharmaceuticals USA, Inc.*, et al., v. *Doctor Reddy's Laboratories Ltd. and Doctor Reddy's Laboratories, Inc.* in the United States District Court for the District of Delaware (Case No. 1:14-cv-01172-GMS).
Nov. 3, 2014 Answer, filed in connection with *Teva Pharmaceuticals USA, Inc., et al.*, v. *Doctor Reddy's Laboratories Ltd. and Doctor Reddy's Laboratories, Inc.* in the United States District Court for the District of Delaware (Case No. 1:14-cv-01172-GMS).
Dec. 1, 2014 Answer to Counterclaims, filed in connection with *Teva Pharmaceuticals USA, Inc., et al.*, v. *Doctor Reddy's Laboratories Ltd. and Doctor Reddy's Laboratories, Inc.* in the United States District Court for the District of Delaware (Case No. 1:14-cv-01172-GMS).
Sep. 11, 2014 Complaint, filed in connection with *Teva Pharmaceuticals USA, Inc., et al.* v. *Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).
Nov. 25, 2014 Plaintiff's Notice of Voluntary Dismissal, filed in connection with *Teva Pharmaceuticals USA, Inc., et al.* v. *Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).
Oct. 6, 2014 Complaint, filed in connection with *Teva Pharmaceuticals USA, Inc., et al.*, v. *Mylan Pharmaceuticals Inc. and Natco Pharma Ltd.* in the United States District Court for the District of Delaware (Case No. 1:14-cv-01278-GMS).
Oct. 7, 2014 Complaint, filed in connection with *Teva Pharmaceuticals USA, Inc., et al.*, v. *Mylan Pharmaceuticals Inc., Mylan Inc. and Natco Pharma Ltd.* in the United States District Court for the Northern District of West Virginia (Case. No. 1:14- cv-00167-IMK).
Nov. 26, 2014 Answer, filed in connection with *Teva Pharmaceuticals USA, Inc., et al.*, v. *Mylan Pharmaceuticals inc., Mylan Inc. and Natco Pharma Ltd.* in the United States District Court for the Northern District of West Virginia (Case. No. 1:14- cv-00167-IMK).
Nov. 18, 2014 Complaint, filed in connection with *Teva Pharmaceuticals USA, Inc., et al.*, v. *Synthon Pharmaceuticals Inc., et al.* in the United States District Court for the District of Delaware (Case. No. 1:14-cv-01419-UNA).
Jan. 23, 2015 Answer, filed in connection with *Teva Pharmaceuticals USA, Inc., et al.*, v. *Synthon Pharmaceuticals Inc., et al.* in the United States District Court for the District of Delaware (Case. No. 1:14-cv-01419-UNA).
Feb. 17, 2015 Answer to Counterclaims, filed in connection with *Teva Pharmaceuticals USA, Inc., et al.*, v. *Synthon Pharmaceuticals Inc., et al.* in the United States District Court for the District of Delaware (Case. No. 1:14-cv-01419-UNA).
Nov. 19, 2014 Complaint, filed in connection with *Teva Pharmaceuticals USA, Inc., et al.*, v. *Synthon Pharmaceuticals Inc., et al.* in the United States District Court for the Middle District of North Carolina (Case. No. 1:14-cv-975).
Feb. 12, 2015 Plaintiff's Notice of Voluntary Dismissal, filed in connection with *Teva Pharmaceuticals USA, Inc., et al.*, v. *Synthon Pharmaceuticals Inc., et al.* in the United States District Court for the Middle District of North Carolina (Case. No. 1:14-cv-975).
Feb. 3, 2015 Complaint, filed in connection with *Teva Pharmaceuticals USA, Inc., et al.*, v. *Amneal Pharmaceuticals LLC* in the United States District Court for the District of Delaware (Case. No. 1:15-cv-00124-GMS).
Costello, K., et al., "Recognizing Nonadherence in Patients with Multiple Sclerosis and Maintaining Treatment Adherence in the Long Term," Medscape J Med., vol. 10(9):225 (2008).
Edgar, C.M., et al., "Lipoatrophy in Patients with Multiple Sclerosis on Glatiramer Acetate," Can. J. Neurol. Sci., vol. 31:58-63 (2004).
Ford, CC., et al. "A Prospective open-label study of glatiramer acetate: over a decade of continuous use in multiple sclerosis patients," Multiple Sclerosis, vol. 12:309-320 (2006).
Gagnon, L., "Every-Other-Day Dosing of Glatiramer Acetate Reduces Adverse Reactions With Comparable Efficacy to Daily Dosing: Presented at WCTRMS," PeerView Press, (Sep. 21, 2008).
Ge, Y., et al. "Glatiramer Acetate (Copaxone) Treatment in Relapsing-Remitting Multiple Sclerosis", Neurology, vol. 54:813-817 (Feb. 2000).
Johnson, K.P., et al., "Copolymer 1 reduces relapse rate and improves disability in relapsing-remitting multiple sclerosis: phase III multicenter, double-blind, placebo-controlled trial," Neurology, vol. 45:1268-1276 (Jul. 1995).
Klauer, T., and Zettl, U.K., "Compliance, adherence, and the treatment of multiple sclerosis," J Neurol. vol. 255 (Suppl. 6) :87-92 (2008).
Lisak, R.P. and Kira, J., "Chapter 100, Multiple Sclerosis," International Neurology, 366-374 (2009).
Manso, P.J., and Sokol, A.L., "Life cycle management of ageing pharmaceutical assets," Pharmaceutical Law Insight, vol. 3(7):16-19 (Jul./Aug. 2007).
Copaxone®, Physicians' Desk Reference, 62nd ed. Montvale, NJ, Thomson Healthcare Inc., pp. 3231-3235 (2008).
Rebif® (interferon beta-la), Product Description, 103795.5062PI final 6.7.05 (2005).
This Is MS Multiple Sclerosis Community: Knowledge & Support [online]. ThisIsMS [retrieved on Sep. 3, 2014]. Retrieved from the Internet: <URL:www.thisisms.com/forum/copaxonef4/topic5610.html>.
Clinical Trial Comparing Treatment of Relapsing-Remitting Multiple Sclerosis (RR-MS) With Two Doses of Glatiramer Acetate (GA) [online]. ClinicalTrials.gov, 1993 [retrieved on Feb. 13, 2015]. Retrieved from the Internet: <URL: clinicaltrials.gov/show/NCT00337779>.
A Study to Test the Effectiveness and Safety of a New Higher 40mg Dose of Copaxone® Compared to Copaxone® 20mg, the Currently Approved Dose [online]. ClinicalTrials.gov, 1993 [retrieved on Feb. 13, 2015]. Retrieved from the Internet: <URL: clinicaltrials.gov/show/NCT00202982>.
Safety and Tolerability of Glatiramer Acetate (GLACIER). ClinicalTrials.gov, 1993 [retrieved on Feb. 19, 2015]. Retrieved from the Internet: <URL:clinicaltrials.gov/ct2/show/NCT01874145>.
Bornstein et al., "A Placebo-controlled, Double-blind, Randomized Two-center, Pilot Trial of Cop 1 in Chronic Progressive Multiple Sclerosis," Neurol., 1991, 41, 533-539.
Bornstein et al., "Rationale for Immunomodulating Therapies of Multiple Sclerosis: Clinical Trial Design in Multiple Sclerosis Therapy," Neurol., 1988, vol. 38 (Suppl.2), pp. 80-81 [R].
Bornstein, "Clinical Experience: Hopeful Prospects in Multiple Sclerosis," Hospital Practice (Off. Ed.), 1992, vol. 27, No. 5, pp. L135-L158, 141-142, 145-158.
Bornstein, "Cop 1 may be Beneficial for Patients with Exacerbating-remitting Form of Multiple Sclerosis," Adv. Ther. (USA), 1987, 4, 206 (Abstract).
Bornstein et al., "Treatment of Multiple Sclerosis with Copolymer 1" in Treatment of Multiple Sclerosis: Trial Design, Results and Future Perspectives (Rudick R.A. & Goodkin D.E., eds., Springer Lerlag, London 1992) 173-198.
Bornstein et al., "A Pilot Trial of Cop 1 in Exacerbating-remitting Multiple Sclerosis," New Eng. J. Med., 1987, 317(7), 408-414.
Bornstein et al., "Clinical Experience with COP-1 in Multiple Sclerosis," Neurol., 1988, 38(Suppl. 2) 66-69.

(56) References Cited

OTHER PUBLICATIONS

Bornstein, et al., "Clinical Trials of a Synthetic Polypeptide (Copolymer 1) for the treatment of Multiple Sclerosis" in Gannett et al., Immunological and Clinical Aspects of Multiple Sclerosis (MTP Press, The Hague, 1984) 144-150.

Bornstein et al., "Clinical Trials of Copolymer 1 in Multiple Sclerosis," Ann. N. Y. Acad. Sci. (USA), 1984, 366-372.

Bornstein et al., "Multiple Sclerosis: Clinical Trials of a Synthetic Polypeptide, Copolymer 1," Neural., 1985, 35, (Suppl. 1), 103 (Abstract).

Bornstein et al., "Multiple Sclerosis: Trial of a Synthetic Polypeptide," Ann. Neurol., 1982, 11, 317-319.

Bornstein et al., "Pilot Trial of COP-1 in Chronic Progressive Multiple Sclerosis: Preliminary Report," from the International Multiple Sclerosis Conference: An Update on Multiple Sclerosis, Roma (Italy), Sep. 15-17, 1988, in Elsevier Science Publisher, 1989, 225-232.

Bornstein et al., "Treatments of Multiple Sclerosis with a Synthetic Polypeptide: Preliminary Results," Ann. Neurol., 1980, 8, 117 (Abstract).

Bornstein et al., "Treatments of Multiple Sclerosis with a Synthetic Polypeptide: Preliminary Results," Trans. Am. Neural. Assoc., 1980, 105, 348-350.

Bornstein et al., "Clinical Trials of Cop 1 in Multiple Sclerosis," in Handbook of Multiple Sclerosis (S.D. Cook Marcel Rekker, ed., 1990) 469-480.

Caon et al., "Randomized, prospective, rater-blinded, four year pilot study to compare the effect of daily versus every other day glatiramer acetate 20 mg subcutaneous injections in RRMS" Neurology, 2009, vol. 72, No. 11, p. A317.

Clinical Trial Protocol No. 9001, Teva Pharmaceutical Industries, Ltd., first patient enrolled Oct. 23, 1991.

Clinical Trial Protocol No. 9002, Lemmon Co. and Teva Pharmaceutical Industries, Ltd., first patient enrolled Jun. 17, 1993.

Cohen et al., "Randomized, double-blind, dose comparison study of glatiramer acetate in relapsing-remitting MS" Neurology, 2007, 68: 939-944.

Cohen et al., "Identifying and treating patients with suboptimal responses" Neurology, 2004, Dec. 28;63(12 Suppl 6):S33-40.

Comi et al. "Treatment with glatiramer acetate delays conversion clinically definite multiple sclerosis (CDMS) in patients with clinically isolated syndromes (CIS)" Neurology 2008; 71 (2): 153.

Comi G, Filippi M. Presented at: 60th Annual Meeting of the American Academy of Neurology: Apr. 12-19, 2008; Chicago, IL. Abstract LBS. 003.

Comi G. "Treatment with glatiramer acetate delays conversion to clinically definite multiple sclerosis (CDMS) in patients with clinically isolated syndromes (CIS)" Program and abstracts of the American Academy of Neurology 60th Annual Meeting; Apr. 12-19, 2008; Chicago, Illinois. LBS.003.

Comi et al. "European/Canadian multicenter, double-blind, randomized, placebo-controlled study of the effects of glatiramer acetate on magnetic resonance imagine-measured disease activity and burden in patients with relapsing multiple sclerosis". Ann Neurol., 2001, 49:290-7.

Cord et al., "Results from a phase III, one-year, randomized, double-blind, parallel-group, dose-comparison study with glatiramer acetate in relapsing-remitting multiple sclerosis". Mult Scler., 2008, 14(suppl 1):S299.

Copaxone, Food and Drug Administration Approved Labeling (Reference ID: 3443331) [online], Teva Pharmaceutical Industries Ltd., 2014 [retrieved on Dec. 24, 2014], Retrieved from the Internet: <URL: www.accessdata.fda.gov/drugsatfda_docs/label/2014/020622s0891b1.pdf>.

Flechter S, et al., "Copolymer 1 (Glatiramer Acetate) in Relapsing Forms of Multiple Sclerosis: Open Multicenter Study of Alternate-Day Adlninistration". Clinical Neuropharmacology, 2002, 25: 11-15.

Flechter S. et al., "Comparison of glatiramer acetate (Copaxone®) and interferon beta-lb (Betaferon®) in multiple sclerosis patients: An open-label 2-year follow up" Journal of the Neurological Sciences, 2002, vol. 197, No. 1-2 pp. 51-55.

Immunological Responses to Different Doses of Glatiramer Acetate in MS: Analyses for the FORTE Trial, Yong W. V., et al., poster session dated Apr. 28, 2009, presented at the 61st Annual American Academy of Neurology meeting in Seattle, Washington U.S.A.

Johnson, et al., "Extended use of glatiramer acetate (Copaxone) is well tolerated and maintains its clinical effect on multiple relapse rate and degree of disability". Neurology. 1998, 50:701-8.

Jul. 7, 2008 Forte Trial Update by Teva Pharmaceutical Industries Ltd.

Khan et al., "Randomized, prospective, rater-blinded, four-year, pilot study to compare the effect of daily versus every-other-day injections in relapsing-remitting multiple" Mult. Scler. 2008, 14 Suppl. 1 S296.

Khan et al., "Glatiramer acetate 20mg subcutaneous twice-weekly versus daily injections: results of a pilot, prospective, randomised, and rater-blinded clinical and MRI 2-year study in relapsing-remitting multiple sclerosis" Immunomodulation-2; Friday, Sep. 11, 2009.

Khan O. et al., "Randomized, prospective, rater-blinded, four-year, pilot study to compare the effect of daily versus every-other-day glatiramer acetate 20 mg subcutaneous injections in relapsing-remitting multiple sclerosis", Multiple Sclerosis. 2008, 14: 5295-5298.

Khan O. et al., "A phase 3 trial to assess the efficacy and safety of glatiramer acetate injections 40mg administered 3 times a week compared to placebo" European Committee for Treatment and Research in Multiple Sclerosis, 2012.

Martinelli BF, Rovaris M, Johnson KP, Miller A, Wolinsky JS, Ladkani D, Shifroni G, Comi G, Filippi M. Effects of glatiramer acetate on relapse rate and accumulated disability in multiple sclerosis: meta-analysis of three double-blind, randomized, placebo-controlled clinical trials. Mult Scler. Aug. 2003; 9(4):349-55.

Wolinsky, et al., "Glatiramer acetate in primary progressive multiple sclerosis: Results of a multinational, multicenter, double-blind, placebo-controlled trial". Ann Neurol., 2007, 61:14-24.

Wolinsky, JS, "The use of glatiramer acetate in the treatment of multiple sclerosis". Adv Neurol., 2006, 273-92.

U.S. Appl. No. 09/359,099, filed Jul. 22, 1999 (Strominger et al.). The specification and claims as originally filed.

Reissue Application in connection with U.S. Appl. No. 13/964,856, filed Aug. 12, 2013 (Konfino et al.).

File history of U.S. Appl. No. 13/964,856, filed Aug. 12, 2013.

Request for Ex Parte Re-examination by Third Party in connection with U.S. Control No. 90/013,249, filed May 21, 2014 (Konfino et al.).

File history of U.S. Control No. 90/013,249, filed May 21, 2014 (Konfino et al.).

Goossens et al., "Pressure- and temperature-induced unfolding and aggregation of recombinant human interferon-c: a Fourier transform infrared spectroscopy study" Biochem. J. 2003, 370, 529-535

Gursky et al., "Temperature-dependent β-sheet formation in β-amyloid Aβ1-40 peptide in water: uncoupling β-structure folding from aggregation" Biochimica et Biophysica Acta, 2000, 1476 93-102.

Kim et al. "Some Factors Determining Protein Aggregation during Ultrafiltration", Biotechnology and Bioengineering, 1993, vol. 42, pp. 260-265.

Celik et al., "Protein fouling behavior of carbon nanotube/polyethersulfone composite membranes during water filtration" Water Research, 2011, 45:5287-94.

Shinchuk et al. "Poly-(L-Alanine) Expansions Form Core—Sheets that Nucleate Amyloid Assembly" Proteins: Structure, Function, and Bioinformatics, 2005, 61:579-589.

Varkony et al. "The glatiramoid class of immunomodulator drugs" Expert Opin. Pharmacother. 2009, 10(4):1-12.

Vrijenhoek et al., "Influence of membrane surface properties on initial rate of colloidal fouling of reverse osmosis and nanofiltration membranes" Journal of Membrane Science, 2001, 188:115-12B.

May 26, 2015 Yeda's Preliminary Patent Owner Response, filed in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).

(56) References Cited

OTHER PUBLICATIONS

May 26, 2015 Yeda's Preliminary Patent Owner Response, filed in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).

Teva Provides Update on Forte Trial (Jul. 7, 2008), submitted as Exhibit 2001 in Inter Partes Review Case Nos. IPR2015-00643 and IPR2015-00644.

Franscisco J. Quintana et al., Systems Biology Approaches for the Study of Multiple Sclerosis, 12 J.Cell. Mol. Med. 4, 1087-93 (2008), submitted as Exhibit 2002 in Inter Partes Review Case Nos. IPR2015-00643 and IPR2015-00644.

David J. Virley, Developing Therapeutics for the treatment of multiple sclerosis, 2 J. Am. Soc. for Exp. Neurotherapeutics, 638-49 (Oct. 2005), submitted as Exhibit 2003 in Inter Partes Review Case Nos. IPR2015-00643 and IPR2015-00644.

Manuel A. Friese, The value of animal models for drug development in multiple sclerosis, 129 Brain, 1940-52 (2006), submitted as Exhibit 2004 in Inter Partes Review Case Nos. IPR2015-00643 and IPR2015-00644.

Copaxone Prescribing Information (Jan. 2014), submitted as Exhibit 2005 in Inter Partes Review Case Nos. IPR2015-00643 and IPR2015-00644.

Dvora Teitelbaum et al., Suppression of experimental allergic encephalomyelitis by a synthetic polypeptide, 1 Eur. J. Immunol., 242-248 (Aug. 1971), submitted as Exhibit 2006 in Inter Partes Review Case Nos. IPR2015-00643 and IPR2015-00644.

Jill Conner, Glatiramer acetate and therapeutic peptide vaccines for multiple sclerosis, 1 J. Autoimmunity and Cell Responses 3 (2014), submitted as Exhibit 2007 in Inter Partes Review Case Nos. IPR2015-00643 and IPR2015-00644.

Copaxone, Physicians' Desk Reference 62ed. (2008), submitted as Exhibit 2008 in Inter Partes Review Case Nos. IPR2015-00643 and IPR2015-00644.

Wiebke Schrempf and Tjalf Ziemssen, Glatiramer acetate: Mechanisms of action in multiple sclerosis, 6 Autoimmun. Rev., 469-475 (2007), submitted as Exhibit 2009 in Inter Partes Review Case Nos. IPR2015-00643 and IPR2015-00644.

V.Wee Yong, Differential mechanisms of action of interferon-13 β and glatiramer acetate in MS, 59 Neurology, 802-8 (Apr. 2002), submitted as Exhibit 2010 in Inter Partes Review Case Nos. IPR2015-00643 and IPR2015-00644.

Suhayl Dhib-Jalbut, Mechanisms of action of interferons and glatiramer acetate in multiple sclerosis, 58 Neurology (8 Suppl 4), S3-9 (2002), submitted as Exhibit 2011 in Inter Partes Review Case Nos. IPR2015-00643 and IPR2015-00644.

Oliver Neuhaus et al., Pharmacokinetics and pharmacodynamics of the interferon-betas, glatiramer acetate, and mitoxantrone in multiple sclerosis, 259 J. Neurol. Sci., 27-37 (2007), submitted as Exhibit 2012 in Inter Partes Review Case Nos. IPR2015-00643 and IPR2015-00644.

Oded Abramsky et al., Effect of a Synthetic Polypeptide (COP 1) on Patients With Multiple Sclerosis and With Acute Disseminated Encephalomyelitis. Preliminary Report, 31 J. Neurol. Sci., 433-38 (1977), submitted as Exhibit 2013 in Inter Partes Review Case Nos. IPR2015-00643 and IPR2015-00644.

Murry B. Bornstein et al., Treatment of Multiple Sclerosis with a Synthetic Polypeptide: Preliminary Results, 105 Tran. Am. Neurol. Assoc., 348-50 (1980), submitted as Exhibit 2014 in Inter Partes Review Case Nos. IPR2015-00643 and IPR2015-00644.

Murry B. Bornstein et al., Multiple Sclerosis: Trial of a Synthetic Polypeptide, 11 Ann. Neurol., 317-19 (Mar. 1982), submitted as Exhibit 2015 in Inter Partes Review Case Nos. IPR2015-00643 and IPR2015-00644.

Murry B. Bornstein et al., A Pilot Trial of COP 1 in Exacerbating-Remitting Multiple Sclerosis, 13 N. Engl. J. Med., 408-14 (Aug. 13, 1987), submitted as Exhibit 2016 in Inter Partes Review Case Nos. IPR2015-00643 and IPR2015-00644.

Sage Journals, msj.sagepub.com/content/14/1_suppl.toc (Sep. 2008), submitted as Exhibit 2017 in Inter Partes Review Case Nos. IPR2015-00643 and IPR2015-00644.

Massimo Filippi et al., Effects of oral glatiramer acetate on clinical and MRI monitored disease activity in patients with relapsing multiple sclerosis: a multicentre, double-blind, randomised, placebocontrolled study, neurology.thelancet.com (Jan. 20, 2006), submitted as Exhibit 2018 in Inter Partes Review Case Nos. IPR2015-00643 and IPR2015-00644.

Yuval Ramot et al., Comparative Long-Term Preclinical Safety Evaluation of Two Glatiramoid Compounds (Glatiramer Acetate, Copaxonel, and TV-5010, Protiramer) in Rats and Monkeys, 40 Toxicol. Path., 40-54 (2012), submitted as Exhibit 2019 in Inter Partes Review Case Nos. IPR2015-00643 and IPR2015-00644.

U.S. Patent Application No. 2007/0161566 A1 ("Pinchasi"), submitted as Exhibit 2020 in Inter Partes Review Case Nos. IPR2015-00643 and IPR2015-00644.

Tjalf Ziemssen et al., Risk-Benefit Assessment of Glatiramer Acetate in Multiple Sclerosis, 24 Drug Safety, 13, 979-90 (2001), submitted as Exhibit 2021 in Inter Partes Review Case Nos. IPR2015-00643 and IPR2015-00644.

Teva News Release, Phase III Data Published in Annals of Neurology Show That a Higher Concentration Dose of Glatiramer Acetate Given Three Times a Week Reduced Annualized Relapse Rates in the Treatment of Relapsing-Remitting Multiple Sclerosis (Jul. 1, 2013), submitted as Exhibit 2022 in Inter Partes Review Case Nos. IPR2015-00643 and IPR2015-00644.

Omar Khan et al., Three Times Weekly Glatiramer Acetate in Relapsing-Remitting Multiple Sclerosis, 73 Ann. Neurol., 705-13 (2013), submitted as Exhibit 2023 in Inter Partes Review Case Nos. IPR2015-00643 and IPR2015-00644.

Teva Press Release, Teva Reports First Quarter 2015 Results (Apr. 30, 2015), submitted as Exhibit 2024 in Inter Partes Review Case Nos. IPR2015-00643 and IPR2015-00644.

Kate McKeage, Glatiramer Acetate 40 mg/mL in Relapsing-Remitting Multiple Sclerosis: A Review, CNS Drugs (Apr. 24, 2015), submitted as Exhibit 2025 in Inter Partes Review Case Nos. IPR2015-00643 and IPR2015-00644.

K.P. Johnson et al., Copolymer 1 reduces relapse rate and improves disability in relapsing-remitting multiple sclerosis: Results of a phase III multicenter, doubleblind, placebo-controlled trial, 45 Neurology, 1268-76 (1995), submitted as Exhibit 2026 in Inter Partes Review Case Nos. IPR2015-00643 and IPR2015-00644.

Feb. 24, 2015 Answer, filed in connection with *Teva Pharmaceuticals USA, Inc., et al.*, v. *Amneal Pharmaceuticals LLC* in the United States District Court for the District of Delaware (Case. No. 1:15-cv-00124-GMS).

Mar. 20, 2015 Answer to Amneal's Counterclaims, filed in connection with *Teva Pharmaceuticals USA, Inc., et al.*, v. *Sandoz Inc. and Amneal Pharmaceuticals LLC*, in the the United States District Court for District of Delaware (Case No. 1:14-cv-01171-GMS).

May 19, 2015 Answer, Affirmative Defenses and Counterclaims of Amneal Pharmaceuticals LLC to Plaintiff's First Amended Complaint for Patent Infringement, in the United States District Court for the District of Delaware (Case No. 1:14-cv-01171-GMS) (Consolidated).

May 21, 2015 Answer, Affirmative Defenses and Counterclaims of Amneal Pharmaceuticals LLC to Plaintiff's First Amended Complaint for Patent Infringement in the United States District Court for the District of Delaware (Case No. 1:14-cv-01171-GMS) (Consolidated).

May 21, 2015 Synthon's Answer, Affirmative Defenses and Counterclaims to Plaintiff's First Amended Complaint for Patent Infringement in the United States District Court for the District of Delaware (Case No. 1:14-cv-01171-GMS) (Consolidated).

May 21, 2015 Sandoz and Momenta Pharmaceuticals, Inc.'s Answer to Complaint for Patent Infringement and Counterclaims in the United States District Court for the District of Delaware (Case No. 1:14-cv-01171-GMS) (Consolidated).

May 21, 2015 DRL's Answer and Counterclaims to First Amended Complaint in the United States District Court for the District of Delaware (Case No. 1:14-cv-01171-GMS) (Consolidated).

* cited by examiner

PROCESS FOR MANUFACTURING GLATIRAMER ACETATE PRODUCT

The disclosures of various publications in their entireties are hereby incorporated by reference into this application in order to more fully describe the state of the art to which this invention pertains.

BACKGROUND OF THE INVENTION

Glatiramer acetate (GA), the active ingredient of Copaxone®, consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The peak average molecular weight of glatiramer acetate is between 5,000 and 9,000 daltons. Glatiramer acetate is identified by specific antibodies (Copaxone, Food and Drug Administration Approved Labeling (Reference ID: 3443331) [online], TEVA Pharmaceutical Industries Ltd., 2014 [retrieved on Dec. 24, 2014], Retrieved from the Internet: <URL: www.accessdata.fda.gov/drugsatfda_docs/label/2014/020622s0891bl.pdf>).

Chemically, glatiramer acetate is designated L-glutamic acid polymer with L-alanine, L-lysine and L-tyrosine, acetate (salt). Its structural formula is:

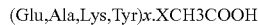
(Glu,Ala,Lys,Tyr)$_x$.XCH3COOH

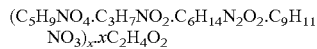
($C_5H_9NO_4.C_3H_7NO_2.C_6H_{14}N_2O_2.C_9H_{11}NO_3$)$_x$.x$C_2H_4O_2$

CAS-147245-92-9

Copaxone® is a clear, colorless to slightly yellow, sterile, nonpyrogenic solution for subcutaneous injection. Each 1 mL of Copaxone® solution contains 20 mg or 40 mg of GA, the active ingredient, and 40 mg of mannitol. The pH of the solutions is approximately 5.5 to 7.0. Copaxone® 20 mg/mL in a prefilled syringe (PFS) is an approved product, the safety and efficacy of which are supported by over two decades of clinical research and over a decade of post-marketing experience. Copaxone® 40 mg/mL in a PFS was developed as a new formulation of the active ingredient GA. Copaxone® 40 mg/mL is a prescription medicine used for the treatment of people with relapsing forms of multiple sclerosis (Copaxone, Food and Drug Administration Approved Labeling (Reference ID: 3443331) [online], TEVA Pharmaceutical Industries Ltd., 2014 [retrieved on Dec. 24, 2014], Retrieved from the Internet: <URL: www.accessdata.fda.gov/drugsatfda_docs/label/2014/020622s0891bl.pdf>).

It is an object of the present invention to provide an improved process for manufacturing GA drug products.

SUMMARY OF THE INVENTION

The patent provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

This patent also provides a prefilled syringe containing 40 mg of glatiramer acetate and 40 mg mannitol, which syringe is prepared by a process of the invention.

This patent further provides an aqueous pharmaceutical solution comprising 40 mg/ml glatiramer acetate and 40 mg/ml mannitol, wherein the aqueous pharmaceutical solution
a) has a viscosity in the range of 2.0-3.5 cPa; or
b) has an osmolality in the range of 275-325 mosmol/Kg.

This patent also provides a prefilled syringe containing 1 ml of an aqueous pharmaceutical solution prepared by a process of the invention.

This patent also provides an automated injector comprising the prefilled syringe prepared by a process of the invention.

Aspects of the present invention relate to a method of treatment of a human patient suffering from a relapsing form of multiple sclerosis comprising administration to the human patient of three subcutaneous injections of a 40 mg/ml dose of glatiramer acetate per week using the prefilled syringe of this invention, using the aqueous pharmaceutical solution of this invention, or using the automated injector of this invention so as to treat the human patient.

DETAILED DESCRIPTION OF THE INVENTION

Figure 1:
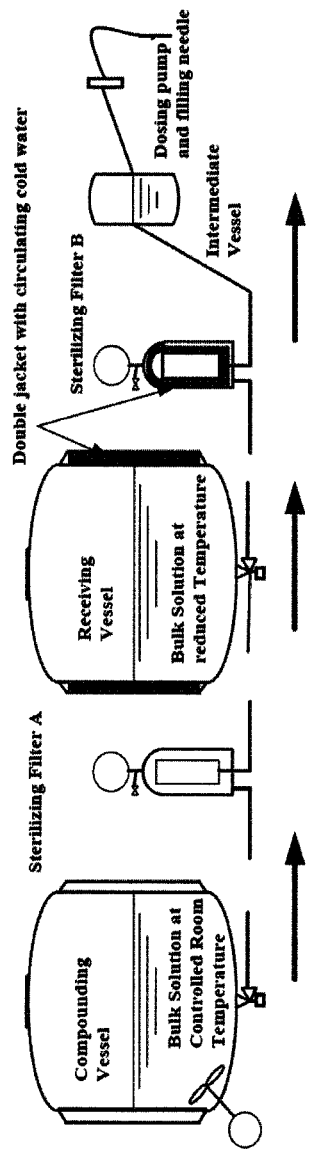
FIG. 1. Schematic description of filtration process by cooled receiving vessel and filter housing.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In some embodiments the filtering step (ii) comprises filtering the aqueous pharmaceutical solution through a first filter, or a first filter and a second filter.

In some embodiments the process further comprises the step of reducing the temperature of the second filter to a temperature from above 0° C. up to 17.5° C.

In some embodiments the process further comprises the step of reducing the temperature of the aqueous pharmaceutical solution to a temperature from above 0° C. up to 17.5° C. before passing through the second filter.

In some embodiments the filtering step (ii) further comprises the step of receiving the aqueous pharmaceutical solution filtered through the first filter in a receiving vessel.

In some embodiments the process further comprises the step of reducing the temperature of the aqueous pharmaceutical solution to a temperature from above 0° C. up to 17.5° C. after leaving the receiving vessel and before entering into the second filter.

In some embodiments the process further comprises the step of reducing the temperature of the aqueous pharmaceutical solution to a temperature from above 0° C. up to 17.5° C. while in the receiving vessel.

In some embodiments the process further comprises the step of reducing the temperature of the first filter to a temperature from above 0° C. up to 17.5° C.

In some embodiments the process further comprises the step of reducing the temperature of the aqueous pharmaceutical solution to a temperature from above 0° C. up to 17.5° C. before passing through the first filter.

In some embodiments the obtaining step (i) comprises compounding the aqueous pharmaceutical solution in a compounding vessel.

In some embodiments the process further comprises the step of reducing the temperature of the aqueous pharmaceutical solution to a temperature from above 0° C. up to 17.5° C. after leaving the compounding vessel and before entering into the first filter.

In some embodiments the process further comprises the step of reducing the temperature of the aqueous pharmaceutical solution to a temperature from above 0° C. up to 17.5° C. while in the compounding vessel.

In some embodiments the aqueous pharmaceutical solution is passed through the second filter at a rate of 3-25 liters/hour.

In some embodiments the aqueous pharmaceutical solution is passed through the second filter preferably at a rate of 3-22 liters/hour.

In some embodiments the aqueous pharmaceutical solution is passed through the second filter more preferably at a rate of 3-15 liters/hour.

In some embodiments the aqueous pharmaceutical solution is passed through the second filter at a rate more preferably at a rate of 3-10 liters/hour.

In some embodiments the pressure during the filtering step (ii) and the pressure during the filling step (iii) is maintained below 5.0 bar.

In some embodiments the pressure during the filtering step (ii) and the pressure during the filling step (iii) is maintained preferably below 3.0 bar.

In some embodiments the pressure during the filtering step (ii) and the pressure during the filling step (iii) is maintained below 2.0 bar.

In some embodiments the temperature of the aqueous pharmaceutical solution is between 0° C. and 14° C., or the temperature of the aqueous pharmaceutical solution is reduced to a temperature between 0° C. and 14° C.

In some embodiments the temperature of the aqueous pharmaceutical solution is between 0° C. and 12° C., or the temperature of the aqueous pharmaceutical solution is reduced to a temperature between 0° C. and 12° C.

In some embodiments the temperature of the aqueous pharmaceutical solution is 2° C.-12° C., or the temperature of the aqueous pharmaceutical solution is reduced to 2° C.-12° C.

In some embodiments the temperature of the aqueous pharmaceutical solution is 4° C.-12° C., or the temperature of the aqueous pharmaceutical solution is reduced to 4° C.-12° C.

In some embodiments the filtering is performed using a sterilizing filter having a pore size of 0.2 µm or less, wherein the first, the second or both filters are a sterilizing filter having a pore size of 0.2 µm or less.

In some embodiments the pharmaceutical preparation in the suitable container is an aqueous pharmaceutical solution comprising 20 mg/ml glatiramer acetate and 40 mg/ml mannitol.

In some embodiments the pharmaceutical preparation in the suitable container is an aqueous pharmaceutical solution comprising 40 mg/ml glatiramer acetate and 40 mg/ml mannitol.

In some embodiments the pharmaceutical preparation in the suitable container is an aqueous pharmaceutical solution having a pH in the range of 5.5-7.0.

In some embodiments the pharmaceutical preparation in the suitable container is an aqueous pharmaceutical solution which is a sterilized aqueous solution which has been sterilized by filtration and without subjecting the aqueous pharmaceutical solution to heat, chemicals, or radiation exposure.

In some embodiments the pharmaceutical preparation is a lyophilized powder of glatiramer acetate and mannitol.

In some embodiments the process further comprises a step of lyophilizing the filtrate after it has been filled into the suitable container so as to form a lyophilized powder of glatiramer acetate and mannitol in the suitable container.

In some embodiments the suitable container is a syringe, vial, ampoule, cartridge or infusion.

In some embodiments the suitable container is a syringe.

In some embodiments the syringe contains 1ml of an aqueous pharmaceutical solution.

This invention provides a prefilled syringe containing 40 mg of glatiramer acetate and 40 mg mannitol, which syringe is prepared by a process of the invention.

According to any embodiment of the prefilled syringe disclosed herein, the prefilled syringe contains 1 ml of an aqueous pharmaceutical solution of 40 mg/ml of glatiramer acetate and 40 mg/ml mannitol.

According to any embodiment of the prefilled syringe disclosed herein, the aqueous pharmaceutical solution
  a) has a viscosity in the range of 2.0-3.5 cPa; or
  b) has an osmolality in the range of 270-330 mosmol/Kg.

According to any embodiment of the prefilled syringe disclosed herein, the aqueous pharmaceutical solution
  a) has a viscosity in the range of 2.2-3.0 cPa; or
  b) has an osmolality in the range of 275-325 mosmol/Kg.

This invention provides an aqueous pharmaceutical solution comprising 40 mg/ml glatiramer acetate and 40 mg/ml mannitol, wherein the aqueous pharmaceutical solution
  a) has a viscosity in the range of 2.0-3.5 cPa; or
  b) has an osmolality in the range of 275-325 mosmol/Kg.

According to some embodiments of the aqueous pharmaceutical solution, the aqueous pharmaceutical solution has a viscosity in the range of 2.0-3.5 cPa.

According to some embodiments of the aqueous pharmaceutical solution, the aqueous pharmaceutical solution has a viscosity in the range of 2.61-2.92 cPa.

According to some embodiments of the aqueous pharmaceutical solution, the aqueous pharmaceutical solution has an osmolality in the range of 275-325 mosmol/Kg.

According to some embodiments of the aqueous pharmaceutical solution, the aqueous pharmaceutical solution has an osmolality in the range of 300-303 mosmol/Kg.

According to some embodiments of the aqueous pharmaceutical solution, the aqueous pharmaceutical solution comprises glatiramer acetate having a viscosity in the range of 2.3-3.2 cPa.

According to some embodiments of the aqueous pharmaceutical solution, the aqueous pharmaceutical solution comprises glatiramer acetate having a viscosity in the range of 2.6-3.0 cPa.

According to some embodiments of the aqueous pharmaceutical solution, the aqueous pharmaceutical solution comprises glatiramer acetate having an osmolality in the range of 290-310 mosmol/Kg.

According to some embodiments of the aqueous pharmaceutical solution, the aqueous pharmaceutical solution comprises glatiramer acetate having an osmolality in the range of 295-305 mosmol/Kg.

According to some embodiments of the aqueous pharmaceutical solution, the aqueous pharmaceutical solution has a pH in the range of 5.5-7.0.

This invention provides a prefilled syringe containing 1 ml of an aqueous pharmaceutical solution prepared by the invention.

This invention provides an automated injector comprising the prefilled syringe prepared by the invention.

This invention provides a method of treatment of a human patient suffering from a relapsing form of multiple sclerosis comprising administration to the human patient of three subcutaneous injections of a 40 mg/ml dose of glatiramer acetate per week using the prefilled syringe of this invention, using the aqueous pharmaceutical solution of this invention, or using the automated injector of this invention so as to treat the human patient.

In some embodiments, the human patient is suffering from relapsing-remitting multiple sclerosis.

In some embodiments, the human patient has experienced a first clinical episode and has MRI features consistent with multiple sclerosis.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the obtaining step (i) comprises compounding the aqueous pharmaceutical solution in a compounding vessel.

In an embodiment, the process further comprises the step of reducing the temperature of the aqueous pharmaceutical solution to a temperature from above 0° C. up to 17.5° C. while in the compounding vessel.

In an embodiment, the process further comprises the step of reducing the temperature of the first filter to a temperature from above 0° C. up to 17.5° C.

In an embodiment, the process further comprises the step of reducing the temperature of the second filter to a temperature from above 0° C. up to 17.5° C.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the obtaining step (i) comprises compounding the aqueous pharmaceutical solution in a compounding vessel.

In an embodiment, the process further comprises the step of reducing the temperature of the aqueous pharmaceutical solution to a temperature from above 0° C. up to 17.5° C. after leaving the compounding vessel and before entering into the first filter.

In an embodiment, the process further comprises the step of reducing the temperature of the first filter to a temperature from above 0° C. up to 17.5° C.

In an embodiment, the process further comprises the step of reducing the temperature of the second filter to a temperature from above 0° C. up to 17.5° C.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the process further comprises the step of reducing the temperature of the second filter to a temperature from above 0° C. up to 17.5° C.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the process further comprises the step of reducing the temperature of the first filter to a temperature from above 0° C. up to 17.5° C.

In an embodiment, the process further comprises the step of reducing the temperature of the second filter to a temperature from above 0° C. up to 17.5° C.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the obtaining step (i) comprises compounding the aqueous pharmaceutical solution in a compounding vessel.

In an embodiment, the process further comprises the step of reducing the temperature of the aqueous pharmaceutical solution to a temperature from above 0° C. up to 17.5° C. while in the compounding vessel.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the filtering step (ii) further comprises the step of receiving the aqueous pharmaceutical solution filtered through the first filter in a receiving vessel.

In an embodiment, the process further comprises the step of reducing the temperature of the aqueous pharmaceutical solution to a temperature from above 0° C. up to 17.5° C. while in the receiving vessel.

Automated Injection Device

The mechanical workings of an automated injection assisting device can be prepared according to the disclosure in European application publication No. EP0693946 and U.S. Pat. No. 7,855,176, which are incorporated herein by reference.

All combinations of the various elements described herein are within the scope of the invention.

DEFINITIONS

As used herein, "glatiramer acetate" is a complex mixture of the acetate salts of synthetic polypeptides, containing four naturally occurring amino acids: L-glutamic acid, L-alanine, L-tyrosine, and L-lysine. The peak average molecular weight of glatiramer acetate is between 5,000 and 9,000 daltons.

Chemically, glatiramer acetate is designated L-glutamic acid polymer with L-alanine, L-lysine and L-tyrosine, acetate (salt). Its structural formula is:

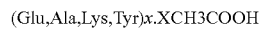

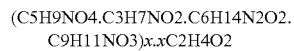

CAS-147245-92-9

As used herein "glatiramer acetate drug substance" is the glatiramer acetate active ingredient prior to its formulation into a glatiramer acetate drug product.

As used herein, a "glatiramer acetate drug product" is a formulation for pharmaceutical use which contains a glatiramer acetate drug substance. Copaxone is a commercial glatiramer acetate drug product manufactured by TEVA Pharmaceutical Industries Ltd. (Israel), which is described in Copaxone, Food and Drug Administration Approved Labeling (Reference ID: 3443331) [online], TEVA Pharmaceutical Industries Ltd., 2014 [retrieved on Dec. 24, 2014], Retrieved from the Internet: <URL: www.accessdata.fda.gov/drugsatfda_docs/label/2014/020622s0891bl.pdf>, the contents of which are hereby incorporated by reference. Copaxone® is available as 20 mg/mL administered once per day, and/or 40 mg/ml administered three times per week.

As used herein, a "sterilizing filter" is a filter with a pore size of 0.2 μm or less which will effectively remove microorganisms.

By any range disclosed herein, it is meant that all hundredth, tenth and integer unit amounts within the range are specifically disclosed as part of the invention. Thus, for example, 1 mg to 50 mg means that 1.1, 1.2 . . . 1.9; and 2, 3 . . . 49 mg unit amounts are included as embodiments of this invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Methods

Glatiramer Acetate (GA) Injection 40 mg/mL in a prefilled syringe (GA injection 40 mg/mL in PFS or Copaxone® 40 mg/mL) was developed as a new formulation of the active ingredient glatiramer acetate, which is also used in the marketed product Copaxone® 20 mg/mL solution for injection in a prefilled syringe. Copaxone® 40 mg/mL is to be administered three times a week by subcutaneous injection to patients with Relapsing Remitting Multiple Sclerosis. The new formulation is based on the formulation of the marketed Copaxone® 20 mg/mL solution for injection in a prefilled syringe. Copaxone® 20 mg/mL is an approved product, the safety and efficacy of which are supported by over two decades of clinical research and over a decade of post-marketing experience. The only difference between the formulations is the double amount of the active substance used, which results in a solution with double the concentration of glatiramer acetate (40 mg/mL vs. 20 mg/mL). The amount of mannitol in both Copaxone® formulations remains unchanged (40 mg/mL).

The compositions of Copaxone® 20 mg/mL and Copaxone® 40 mg/mL are detailed in Table 1.

TABLE 1

Compositions of Copaxone® 20 mg/mL and Copaxone® 40 mg/mL

| Components | Copaxone® 20 mg/mL | Copaxone® 40 mg/mL |
|---|---|---|
| | Content per mL | |
| Glatiramer Acetate[1] | 20.0 mg | 40.0 mg |
| Mannitol USP/Ph.Eur. | 40.0 mg | 40.0 mg |
| Water for Injection USP/Ph.Eur/JP | q.s. to 1.0 mL | q.s. to 1.0 mL |

[1]Calculated on the dry basis and 100% assay

1. Calculated on the Dry Basis and 100% Assay

Studies were conducted in order to verify that the formulation of Copaxone® 40 mg/mL, its manufacturing process and chemical, biological and microbiological attributes are appropriate for commercialization. Studies were also conducted to confirm the suitability of the proposed container closure system for packaging Copaxone® 40 mg/mL.

Mannitol was chosen as the tonicity agent for the initially formulated Copaxone® (freeze dried product, reconstituted prior to administration) as it is also a bulking agent. When the currently marketed ready-to-use formulation of Copaxone® 20 mg/mL solution for injection prefilled syringe was developed, mannitol was used in this formulation as well, as the osmoregulator. Finally, when the new 40 mg/mL formulation was developed, based on the Copaxone® 20 mg/mL formulation, mannitol remained as the osmoregulator.

Mannitol is widely used in parenteral formulations as an osmoregulator. It is freely soluble in water and stable in aqueous solutions. Mannitol solutions may be sterilized by filtration. In solution, mannitol is not affected by atmospheric oxygen in the absence of catalysts. The concentration of mannitol in the Copaxone® 40 mg/mL is 40 mg/mL. Maintaining the mannitol concentration in Copaxone® 40 mg/mL resulted in an essentially isotonic solution.

Water for injection (WFI) is the most widely used solvent and inert vehicle in parenteral formulations. Water is chemically stable in all physical states. It is the base for many biological life forms, and its safety in pharmaceutical formulations is unquestioned.

Example 1

The manufacturing process of Copaxone® 40 mg/mL comprises:
  Compounding a bulk solution of GA and mannitol in water for injections (WFI).
  Sterilizing filtration of the bulk solution yielding the sterile GA solution in bulk.
  Aseptic filling of sterile bulk solution into syringe barrels and stoppering.
  Inspection and final assembly of the filled syringes.

Initially, filtration of bulk solution from the compounding vessel was performed through a sequential filter train consisting of two sequential sterilizing filters (filters named $A_1$ and $A_2$, respectively) to a receiving vessel. From the receiving vessel it was transferred to the intermediate vessel in the filling machine and further through dosing pumps and needles into prefilled syringes. However, due to a Health Authority request to place the sterilizing filter as close as possible to the filling point, the second sterilizing filter was moved between the receiving and intermediate vessels. In the current filtration train, the first sterilizing filter was named Filter A, and the second relocated sterilizing filter was named Filter B. See, FIG. 1.

In line with the process for the approved Copaxone® 20 mg/mL formulation, all processing steps of the new Copaxone® 40 mg/mL formulation were originally conducted at controlled room temperature. However, filtration of the higher concentration solution resulted in a pressure build-up on the second filter, Filter B. Despite the observed pressure increase on Filter B, a high-quality drug product could be obtained by filtration of GA 40 mg/mL at controlled room temperature, as confirmed by release and stability data. Nevertheless, an improved filtration process was needed which avoided the build-up on the second filter.

Flow rate for fluids can be defined by the differential pressure, and inversely moderated by viscosity. Viscosity, in turn, is usually reciprocal in relation to temperature (Meltzer and Jornitz, *Filtration and Purification in the Biopharmaceutical Industry*, Second Edition, CRC Press, 2007, page 166). Increasing the temperature of a solution will normally decrease the viscosity, thereby enhancing the flow rate.

In an attempt to solve the pressure build-up problem on the second filter, the temperature condition of the filtration was raised above controlled room temperature. Although the viscosity decreased, the filterability decreased, resulting in a failed attempt.

The following studies were performed:
  Filter Validation Study: Determination of ranges for the manufacturing parameters related to sterilizing Filter A and sterilizing Filter B of the bulk solution, as well as confirmation of filter compatibility with the drug product.
  Filtration Process: Selection of the sterilizing filtration conditions best suitable for the manufacturing process and the quality of the drug product.

Filters Used for Copaxone® 20 mg/mL and Copaxone® 40 mg/mL Manufacturing

The manufacturing process of Copaxone® 40 mg/mL was based on the process used to produce the marketed Copaxone® 20 mg/mL solution for injection in a prefilled syringe. Therefore the same filters used for filtration of marketed product were used.

Two sterilizing filters were used, each of which having a pore size of 0.2 μm or less, to effectively remove microorganisms. Sterilization is achieved only by filtration using sterilizing filters and not by using other methods, e.g. sterilization is achieved without using heat, chemicals, or radiation exposure.

Filter Validation Study

Confirmation and Setting of Parameters Associated with Filter Compatibility and with Sterilizing Filtration The following tests were performed in order to confirm the filter validity:

Extractables testing—assessment of extractables released from the filter upon steam sterilization and their removal from the filter by a model solvent, thus assessing the volume to be discarded after the filtration through the Filter B, prior to beginning of the aseptic filling.

Compatibility/adsorption testing—assessment of the chemical compatibility of GA 20 mg/mL and GA 40 mg/mL solution with the filter material and the extent of its adsorption to the filter, thus assessing the volume to be discarded after the filtration through Filter B, prior to beginning of the aseptic filling in order to provide assay within specifications.

Residual effect—To ensure that no significant residual GA 20 mg/mL or GA 40 mg/mL solution that might affect the post use integrity test remains on the filter after filtration.

Bacterial challenge—To ensure that the filtration process does not affect the ability of the filter to provide a sterile solution.

The above tests were conducted using maximum pressure (up to 5.0 bar). The validation study demonstrated that the selected filtration system is capable of providing a high quality Copaxone® 20 mg/mL and Copaxone® 40 mg/mL.

Given the strict and well-defined operational and equipment parameters of the GA 40 mg/mL solution filtration process, a plan to mitigate the potential increase in pressure by reducing the filtration temperature was developed.

Without much expectations, it was decided to examine the filtration process of GA 40 mg/mL sterile bulk solution through Filter B under reduced temperature conditions, using the same filters and filtration train as for the filtration at controlled room temperature.

Accordingly, experiments were performed in order to compare the filtration of GA 40 mg/mL sterile bulk solution through Filter B under reduced temperature and controlled room temperature in the production environment and to ensure that there is no difference with regard to the quality and stability profiles of the filtered solutions. In all experiments, the sterile bulk solution was prepared according to the standard compounding and filtration train (see FIG. 1) and filtered through two filters: Filter A and Filter B.

Figure 2:
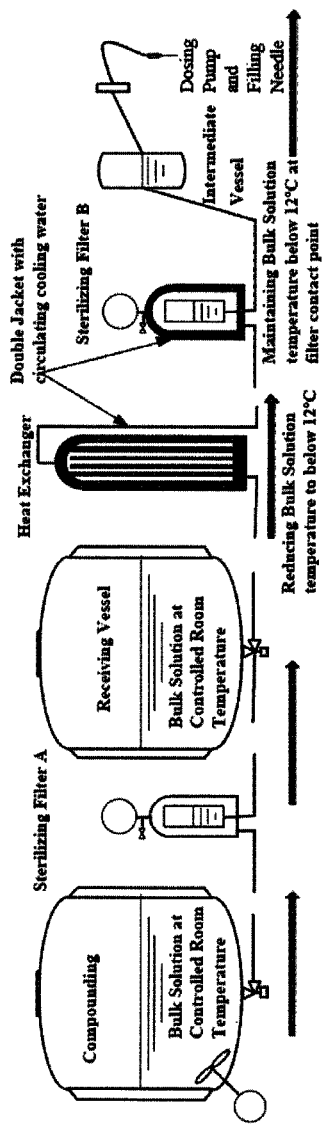
FIG. 2. Schematic description of filtration process by heat exchanger and cooled filter housing.

The experiments tested two different cooling technologies (cooled receiving vessels vs heat exchanger) with cooled filter. The studies are schematically depicted in FIG. 1 and FIG. 2. Further details about these experiments and their outcomes are provided hereafter.

Filtration Process

Experiment No. 1

The objective of Experiment No. 1 was to compare the filterability of a batch of bulk solution held and filtered through Filter B at either controlled room temperature or under reduced temperature conditions (cooling by double-jacketed receiving vessel and cooled Filter B housing).

Figure 3:
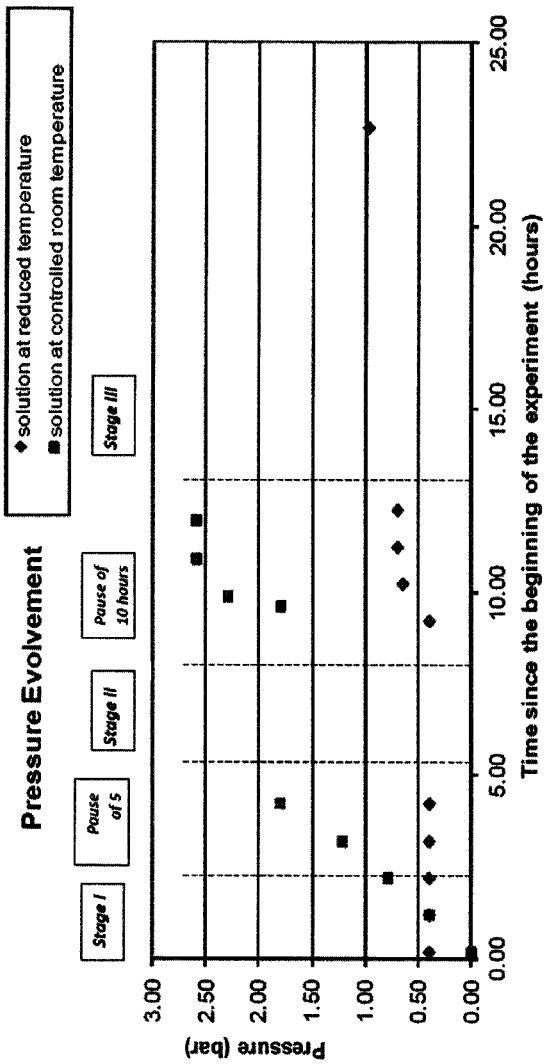
FIG. 3. Pressure record for Experiment No. 1. * Filtration of GA solution at controlled room temperature was stopped and the remaining solution was transferred to the cooled receiving vessels.

The study is schematically depicted in FIG. 1. The experimental design and the obtained results are summarized in Table 2 and FIG. 3.

TABLE 2

Experimental Design and Results for Experiment No. 1.

| Experiment Outline | Reduced Temperature Filtration | Controlled Room Temperature Filtration |
|---|---|---|
| Compounding | According to standard manufacturing procedure[1] | |
| Holding time in the receiving vessel | 13 hours | 13 hours |
| Temperature of solution held in the receiving vessel | 6.6-10.7° C.[2] | 17.8-24.6° C. |
| Planned regimen for filtration though Filter B[3] | Intermittent filtration: Stage I - 5 filtration steps of filtration of about 10 liters of bulk solution - followed by pauses of about 50 minutes each, followed by a pause of 5 hours. Stage II - 4 filtration steps of filtration of about 10 liters of bulk solution - followed by pauses of about 50 minutes each, followed by a pause of about 10 hours. Stage III - Filtration of remaining solution. | |
| Total volume of bulk solution filtered | About 125 L. Filtration was completed. | About 85 liters. Filtration was stopped due to increase in pressure on FilterB. |

[1]One bulk solution was prepared and divided into two portions. Bulk solution size: 230 liters. Filtration of solution at controlled room temperature was stopped after 85 liters have been pushed through the filter due to increased pressure and the remaining solution was transferred to the cooled receiving vessels.
[2]The temperature increased (to 14.9° C.) once during the filtration following the addition of the remaining solution kept at ambient temperature.
[3]The filtrations were carried out in parallel.

Surprisingly, filtration at reduced temperature allowed filtration to be completed without the pressure increase associated with filtration at controlled room temperature.

Example 2

Filtration Process

Experiment No. 2

The first objective of Experiment No. 2 was to evaluate whether local cooling of GA 40 mg/mL solution using a Heat Exchanger (HE) could improve the filterability through cooled Filter B compared to filterability of the same bulk solution at controlled room temperature.

The second objective of Experiment No. 2 was to confirm that there is no difference in the quality of the drug product filled into syringes at controlled room temperature and drug product filled into syringes at reduced temperature.

Cooling by heat exchanger was evaluated as it seemed to be much easier to steam sterilize than using the double jacketed receiving vessels. The HE was located between the receiving vessel and Filter B. Consequently, as opposed to Experiment No. 1 (in which the solution was cooled by the double-jacketed receiving vessels following filtration through Filter A and kept cooled prior to filtration through Filter B), the solution in this experiment was held at controlled room temperature prior to filtration of the locally cooled (by HE) GA solution through Filter B.

Figure 4:
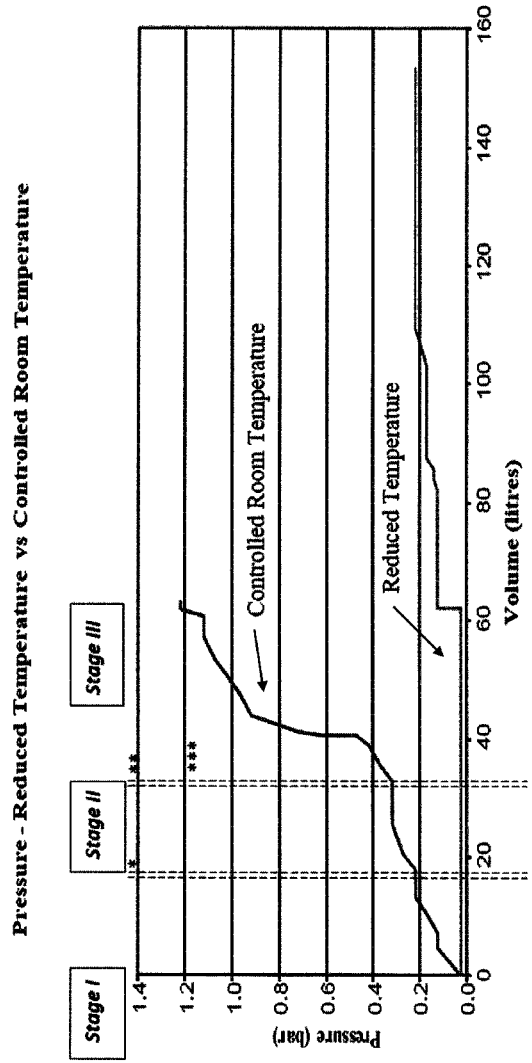
FIG. 4. Pressure record for Experiment No. 2. * Pauses of 3 hours and 5 hours for GA solutions filtered at controlled room temperature and at reduced temperature, respectively.  Pause of 10 hours for both GA solutions. * Filtration of GA solution at controlled room temperature was stopped. Remaining GA solution was filtered at reduced temperature.
Figure 5:
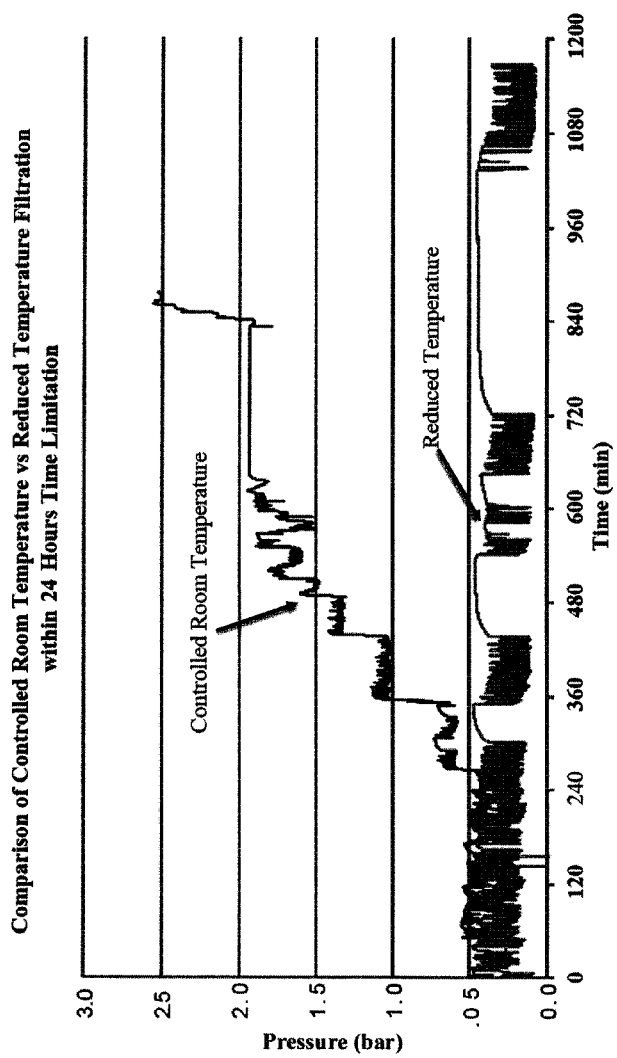
FIG. 5. Pressure record for Experiment No. 3.

The study is schematically depicted in FIG. 2. The experimental design and the obtained results are summarized in Table 3. The pressure observed over the course of the filling process of Experiment No. 2 is shown in FIG. 4.

TABLE 3

Experimental Design and Results for Experiment No. 2.

| Experiment Outline | Reduced Temperature Filtration | Controlled Room Temperature Filtration |
|---|---|---|
| Compounding | According to standard manufacturing procedure[1] | |
| Filtration into a receiving vessel | Filtration of all the bulk solution through Filter A into a receiving vessel held at controlled room temperature | |
| Temperature of solution held in the receiving vessel | Controlled room temperature | |
| Holding time in the receiving vessel | 19 hours | |

TABLE 3-continued

Experimental Design and Results for Experiment No. 2.

| Experiment Outline | Reduced Temperature Filtration | Controlled Room Temperature Filtration |
|---|---|---|
| Planned regimen for filtration through Filter B | The solution is locally cooled as it is transferred through a HE and filtered through cooled Filter B. Three consecutive filtration and filling stages. About 3 hours break between Stage I and Stage II and about 10 hours break between Stage II and Stage III. | The solution is filtered through Filter B at controlled room temperature. Three consecutive filtration and filling stages. About 5 hours break between Stage I and Stage II and about 10 hours break between Stage II and Stage III. |
| Temperature of solution transferred through the HE | 6.4-12° C. | No use of HE |
| Duration of filtration through Filter B[2] | 24 hours | 19 hours |
| Temperature of solution transferred through Filter B | 5.7-8.8° C. | Ambient temperature |
| Total volume of bulk solution filtered and filled into syringes | 154 L | 63 L[3] |
| Storage conditions during stability studies | Long term (2-8° C.) Accelerated (25° C./60% RH) - completed 6 months Stress (40° C./75% RH) - completed 3 months | |
| Stability data | The stability data showed that the drug product has a similar stability profile when it is filtered at controlled room temperature or under reduced temperature conditions. Both filtration processes demonstrate similar impurity profiles. | |

[1] One bulk solution was prepared and divided into two portions. Bulk solution size: 230 liters.
[2] Both filtration processes (reduced and controlled room temperature) were carried out in parallel for comparison. At each stage, filtration was carried out at controlled room temperature, followed by filtration at reduced temperature.
[3] Filtration of solution at controlled room temperature was stopped due to pressure increase and the remaining solution was filtered at reduced temperature.

Example 3

Filtration Process

Experiment No. 3

One objective of Experiment No. 3 was to confirm whether cooling of GA 40 mg/mL bulk solution prior to filtration, using HE and cooled filter housing, allows filtration and filling of batches of 130 L size within various manufacturing regimens.

Another objective of Experiment No. 3 was to evaluate the influence of holding time at various stages of the manufacturing process on filterability of GA 40 mg/mL.

Another objective of Experiment 3 was to demonstrate with a high degree of assurance that locally cooled GA 40 mg/mL solution filtered through Filter B is not different in its quality and stability profile from GA 40 mg/mL solution filtered through Filter B at controlled room temperature conditions with regard to pre-determined parameters and limits.

A series of three batches of bulk solution, manufactured at various regimens, were prepared. Each bulk solution was prepared from an identical combination of the same three drug substance batches.

The experimental design and results are summarized in Table 4.

TABLE 4

Experimental Design and Results for Experiment No. 3

| Experiment Outline | Reduced Temperature Filtration | Controlled Room Temperature Filtration | Reduced Temperature Filtration | Controlled Room Temperature Filtration |
|---|---|---|---|---|
| Batch No. | A | A-2[1] | B | C |
| Compounding | Standard compounding | Standard compounding | Standard compounding | Standard compounding |
| Batch size | First 130 L from bulk solution A | Remaining 50 L from bulk solution A | 180 L | 180 L |
| Holding time in the compounding vessel[2] | 4 hours | 4 hours (same bulk solution as A) | 8 hours | 3.5 hours |
| Holding time in the receiving vessel[3] | 1.5 hours | 10.5 hours[4] | 16 hours | 13 hours |

TABLE 4-continued

Experimental Design and Results for Experiment No. 3

| Experiment Outline | Reduced Temperature Filtration | Controlled Room Temperature Filtration | Reduced Temperature Filtration | Controlled Room Temperature Filtration |
|---|---|---|---|---|
| Duration of filtration through Filter B | 7 hours | 3 hours | 19.5 hours | 13 hours |
| Total duration of entire process (total holding time) | 12.5 hours | 17.5 hours | 43.5 hours | 29.5 hours |
| Temperature range before Filter B | 10.4-12.2° C. | Controlled room temperature | 10.2-11.7° C. | Controlled room temperature |
| Temperature range after Filter B | 9.3-11.0° C. | Controlled room temperature | 9.0-10.2° C. | Controlled room temperature |
| Maximum pressure before Filter B | 0.6 bar | 0.3 bar | 0.6 bar | 2.5 bar[5] |
| Total volume filled into syringes | 130 L | 50 L | 180 L | 134 L |
| Storage conditions during stability studies | Long term (2-8° C.) Accelerated (25° C./60% RH) Stress (40° C./60% RH) | Stress (40° C./60% RH) | Long term (2-8° C.) Accelerated (25° C./60% RH) Stress (40° C./60% RH) | Long term (2-8° C.) Accelerated (25° C./60% RH) Stress (40° C./60% RH) |
| Stability data and conclusions | Stability data showed that the drug product has a similar stability profile at all three storage conditions, regardless of whether it is filtered at controlled room temperature or under reduced temperature conditions. Both filtration processes result in product having substantially the same degradation and impurity profile at stress conditions. | | | |

[1]Batches A and A-2 are from the same bulk solution. Filter B was replaced with a new filter prior to filtration of A-2.
[2]Compounding and subsequent holding time in the compounding vessel (incl. filtration through filter A).
[3]Time from end of filtration through Filter A to beginning of filtration through Filter B and filling.
[4]Since A-2 was filtered and filled into syringes subsequent to the filtration and filling of A, the stated holding time represents the sum of the holding time of A in addition to the time A-2 was held until the filtration at controlled room temperature was initiated.
[5]Throughout the filling, gradual increase of filtration pressure was required in order to maintain flow rate that would correspond to the rate required for continuous filling.

Based on the results of Experiment No. 3, it was confirmed that local cooling by heat exchanger is sufficient in order to enable filtration of a 130 L batch. In addition, the quality and stability profile of GA 40 mg/mL solutions filtered at controlled room temperature and reduced temperature were found to be substantially identical.

Example 4

Figure 6:
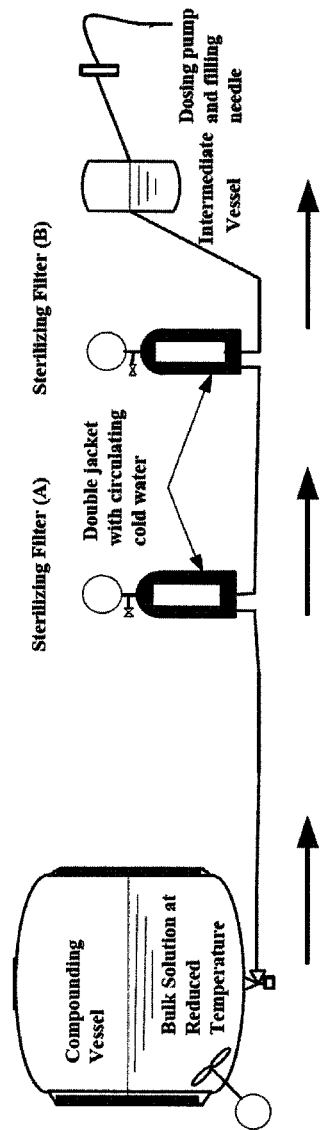
FIG. 6. Schematic description of filtration process by cooled compounding vessel and cooled filter housings on both Filter A and Filter B.

Cooling of GA 40 mg/mL bulk solution below 17.5° C. in the compounding vessel before passing through cooled Filter A and cooled Filter B in sequence (see FIG. 6) results in lower pressure during the filtration step of both Filter A and Filter B as compared to the holding the same bulk solution in the compounding vessel and passing it through Filter A and Filter B at controlled room temperature (Cooling of the bulk solution by using double jacketed compounding vessel and cooling the filters by using double jacketed filter housings).

Reducing the temperature of the GA 40 mg/mL bulk solution in the compounding vessel and passing it through cooled Filter A and Filter B in sequence (see FIG. 6) significantly reduces impairment of filterability caused by the total duration of the process (holding time) as well as by filtering larger volume, compared to the same bulk solution held and filtered under controlled room temperature.

Example 5

Figure 7:
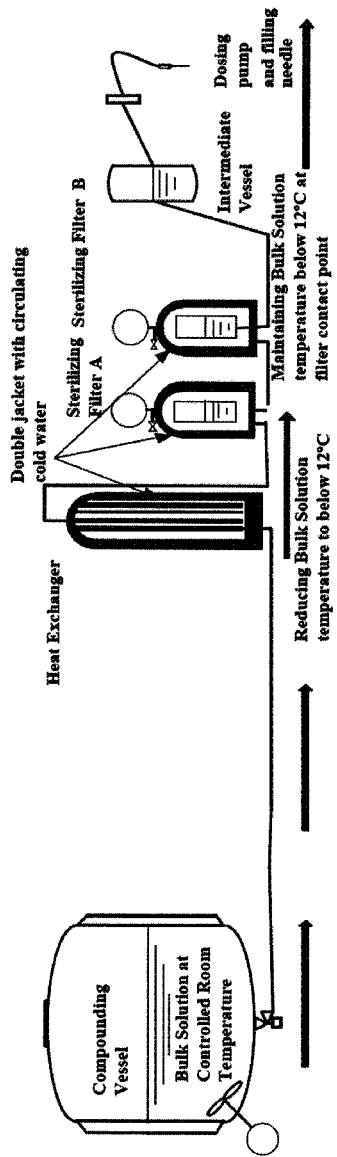
FIG. 7. Schematic description of filtration process by heat exchanger and cooled filter housings on both Filter A and Filter B.

Local cooling of GA 40 mg/mL bulk solution by a heat exchanger and passing the solution through cooled Filter A and cooled Filter B in sequence (see FIG. 7) results in lower pressure during the filtration step of both Filter A and Filter B as compared to passing the same bulk solution held and filtered under controlled room temperature.

Reducing the temperature of the GA 40 mg/mL bulk solution using a heat exchanger and passing it through cooled Filter A and cooled Filter B in sequence (see FIG. 7) significantly reduces impairment of filterability caused by the total duration of the process (holding time) as well as by filtering larger volume, compared to the same bulk solution held and filtered under controlled room temperature.

Example 6

Figure 8:
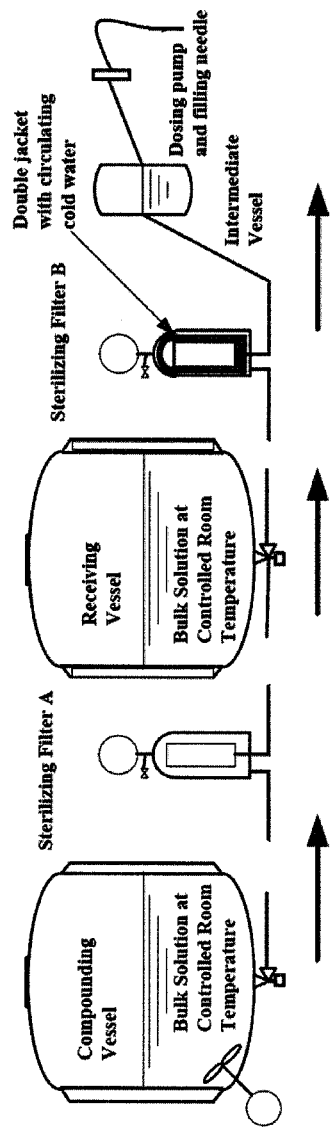
FIG. 8. Schematic description of filtration process by cooled filter housing on only Filter B.

Passing the sterilized GA 40 mg/mL bulk solution from the receiving vessel through cooled Filter B (see FIG. 8) significantly results in lower pressure during the filtration step compared to passing the same bulk solution filtered through Filter B under controlled room temperature.

Passing the sterilized GA 40 mg/mL bulk solution from the receiving vessel through cooled Filter B (see FIG. 8) significantly reduces impairment of filterability caused by the total duration of the process (holding time) as well as by filtering larger volume, compared to the same bulk solution held and filtered under controlled room temperature.

Example 7

Figure 9:
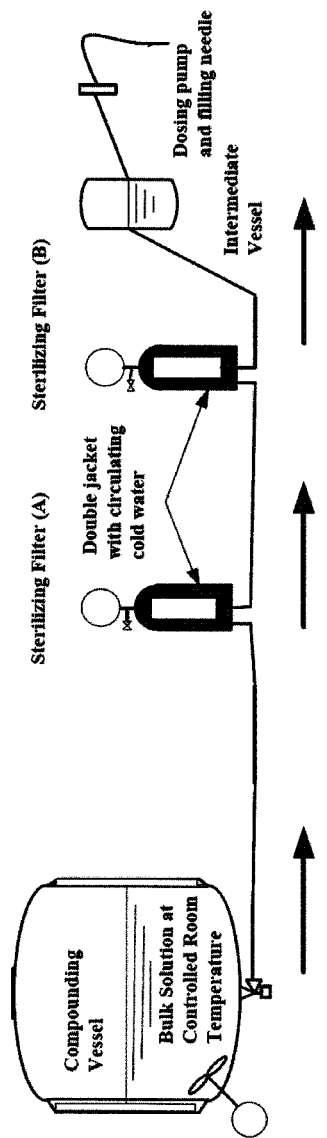
FIG. 9. Schematic description of filtration process by cooled filter housings on both Filter A and Filter B.

Passing GA 40 mg/mL bulk solution from the compounding vessel through cooled Filter A and cooled Filter B in sequence (see FIG. 9) results in lower pressure during the filtration step of both Filter A and Filter B as compared to passing the same bulk solution filtered under controlled room temperature.

Passing GA 40 mg/mL bulk solution from the receiving vessel through cooled Filter A and Filter B in sequence (see FIG. 9) significantly reduces impairment of filterability caused by the total duration of the process (holding time) as well as by filtering larger volume, compared to the same bulk solution filtered under controlled room temperature.

Example 8

Figure 10:
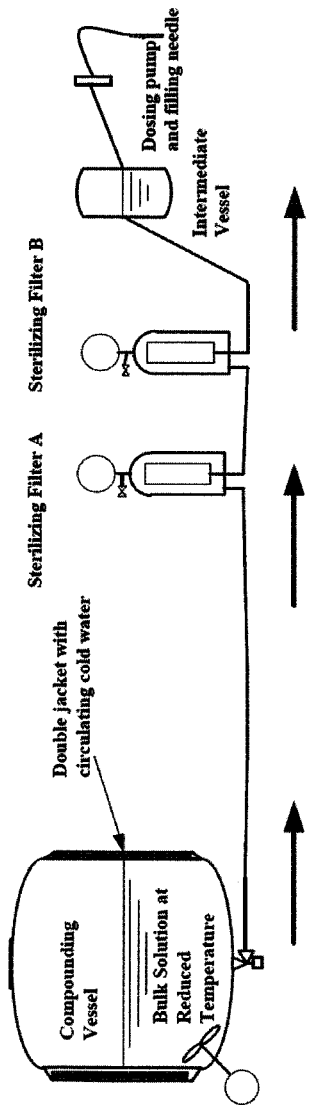
FIG. 10. Schematic description of filtration process by cooled compounding vessel.

Cooling of GA 40 mg/mL bulk solution below 17.5° C. in the compounding vessel before passing through Filter A and Filter B in sequence (see FIG. 10) results in lower pressure during the filtration step of both Filter A and Filter B as compared to the holding the same bulk solution in the compounding vessel and passing it through Filter A and Filter B at controlled room temperature (Cooling of the bulk solution by using double jacketed compounding vessel).

Reducing the temperature of the GA 40 mg/mL bulk solution in the compounding vessel and passing it through Filter A and Filter B in series (see FIG. 10) significantly reduces impairment of filterability caused by the total duration of the process (holding time) as well as by filtering larger volume, compared to the same bulk solution held and under controlled room temperature.

Example 9

Figure 11:
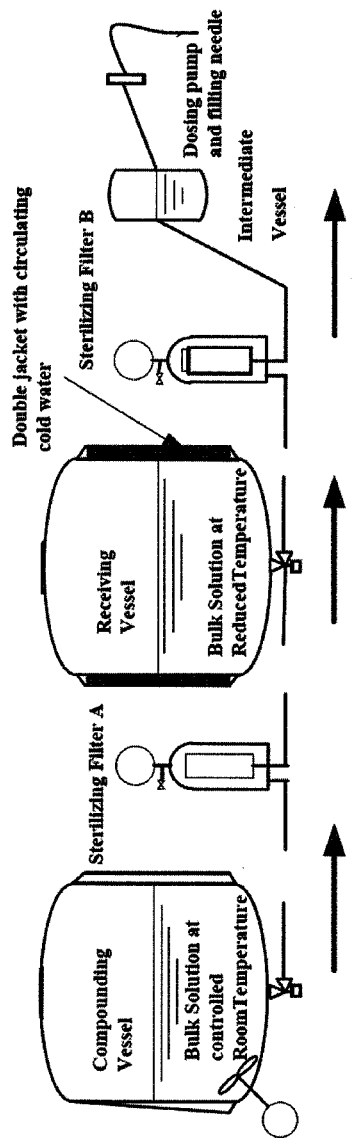
FIG. 11. Schematic description of filtration process by cooled receiving vessel.

Cooling of GA 40 mg/mL bulk solution below 17.5° C. in the receiving vessel before passing through Filter B (see FIG. 11) results in lower pressure during the filtration step of Filter B as compared to the holding the same bulk solution in the compounding vessel at controlled room temperature (Cooling of the bulk solution by using double jacketed compounding vessel).

Reducing the temperature of the GA 40 mg/mL bulk solution in the receiving vessel (see FIG. 10) significantly reduces impairment of filterability caused by the total duration of the process (holding time) as well as by filtering larger volume, compared to the same bulk solution held under controlled room temperature.

Discussion of Examples 1-9

Reducing the temperature of GA 40 mg/mL sterile bulk solution significantly improved its filterability, as demonstrated by the much lower increase in pressure on Filter B during filtration and filling and by the larger volume that can be filtered at reduced temperature. Pressure increases were observed when the sterile bulk solution was held and filtered at controlled room temperature, while there was no significant increase in the pressure when the solution was filtered under reduced temperature conditions.

The holding time of the bulk solution during filtration through Filter B negatively affects the filterability of the solution. However, the total duration of the process (holding time) impaired the filterability significantly less when filtration was performed under reduced temperature conditions. Consequently, longer holding time can be used with reduced temperature filtration.

Both cooling of the solution by passing it through a heat exchanger (local cooling) and/or cooling of the whole bulk (e.g. by double-jacketed receiving vessel) before filtration through cooled Filters A or B or A and B were found to be suitable solutions for reduced temperature filtration.

Accumulated stability data indicate that there is no substantial difference with regard to quality and stability profile between the solution filtered under reduced temperature conditions and the solution filtered at controlled room temperature.

In sum, the performed experiments show that reduced temperature filtration through Filter B significantly improved the filterability of GA 40 mg/mL solution compared to the filterability of the solution when filtered at controlled room temperature. Moreover, reducing the temperature of the bulk solution during the compounding stage or before passing through Filter A, or reducing the temperature of Filter A also improves the filterability of GA 40 mg/mL solution compared to the filterability of the solution at controlled room temperature.

Consequently, the proposed manufacturing process for commercial batches of GA 20 mg/mL and GA 40 mg/mL includes cooling of the solution prior to filtration of the bulk solution through Filter B.

Example 10

Container Closure System

The container closure systems selected for the Copaxone® 40 mg/mL are the same as those used for the marketed product Copaxone® 20 mg/mL PFS. The container closure system consists of a colorless glass barrel, a plastic plunger rod and a grey rubber stopper.

Long Term and Accelerated Stability Studies

Satisfactory stability data after up to 36 months storage under long-term storage conditions (5° C.±3° C.) and after 6 months storage under accelerated conditions (25°±2° C./60±5% RH) are available. The data demonstrate that the proposed container closure systems are suitable for protection and maintenance of the drug product quality throughout its proposed shelf-life.

Protection from Light

Marketed Copaxone® should be stored protected from light. Based on this recommendation, it is proposed that Copaxone® 40 mg/mL be similarly packed in PVC transparent blisters inside a carton box, which provides light protection. The light protection of the proposed packaging when used for the Copaxone® 40 mg/mL is recommended in accordance with the results obtained from a photostability study comparing the following packaging configurations:

1. Glass barrel syringe and plunger rod (Primary package);
   Glass barrel syringe and plunger rod in a transparent blister (partial secondary package);
   Glass barrel syringe and plunger rod in a transparent blister inside carton box (complete intended packaging configuration).

As a reference, the following configurations were added:

2. Glass barrel syringe and plunger rod wrapped in aluminum foil;
   Glass barrel and plunger rod in a transparent blister wrapped in aluminum foil.

All packages were simultaneously exposed to standardized sunlight (5 KLUX) for 10 days and to near UV light for additional 5 days.

All the obtained results from the photostability study are within the specifications. However, the impurity peak detected is lower when the drug product is packed in its complete packaging configuration. The carton box was shown to improve the photostability and gives light protection as good as that of aluminum foil, which is regarded as a complete light protector. The intended packaging configuration is therefore considered suitable for its use.

A storage statement to protect the product from light exposure should be added to the product label.

Microbiological Attributes

The medicinal product is a sterile, single dose, parenteral dosage form. Sterilization is achieved by sterile filtration.

A microbial limits test is performed for the drug substance. The sterility and bacterial endotoxins are monitored upon release and throughout stability studies of the drug product, using pharmacopoeia methods. The limits applied are identical to those applied for the marketed Copaxone®.

The same container closure systems are used for the Copaxone® 20 mg/mL and Copaxone® 40 mg/mL. The integrity testing studies performed to demonstrate the efficacy of the container closure systems on use for the marketed product are also considered relevant for Copaxone® 40 mg/mL.

Example 11

Viscosity

The average viscosity of batches of Copaxone® 20 mg/mL filtered under controlled room temperature and the average viscosity of batches of Copaxone® 40 mg/mL filtered under reduced temperature were obtained and compared. The average viscosity of different batches of Copaxone® 20 mg/mL filtered under controlled room temperature are reported in Table 5. The average viscosity of different batches of Copaxone® 40 mg/mL filtered under reduced temperature are reported in Table 6.

TABLE 5

Viscosity of Batches of Copaxone ® 20 mg/mL Filtered Under Controlled Room Temperature

| Batch No. | Average Viscosity [cPa] | Standard Deviation |
| --- | --- | --- |
| 1 | 1.92[1] | 0.03 |
| 2 | 1.58[1] | 0.00 |
| 3 | 1.58[1] | 0.00 |
| 4 | 1.57[2] | 0.00 |
| 5 | 1.67[2] | 0.01 |
| Water for Injection | 0.93[2] | 0.00 |
| Average | 1.664 | |

[1]Each value is an average of 3 individual results. Values obtained using Rheocalc V2.5 Model LV, Spindle CP40, speed 80 rpm, Shear Rate 600 1/sec, Temperature 25° C. ± 0.1
[2]Each value is an average of 6 individual results. Values obtained using Rheocalc V2.5 Model LV, Spindle CP40, speed 80 rpm, Shear Rate 600 1/sec, Temperature 25° C. ± 0.1

TABLE 6

Viscosity of Batches of Copaxone ® 40 mg/mL Filtered Under Reduced Temperature

| Batch No. | Average Viscosity [cPa][1] | Standard Deviation |
| --- | --- | --- |
| 1 | 2.82 | 0.000 |
| 2 | 2.92 | 0.008 |
| 3 | 2.91 | 0.010 |
| 4 | 2.61 | 0.012 |
| 5 | 2.61 | 0.004 |
| 6 | 2.73 | 0.021 |
| 7 | 2.61 | 0.016 |
| Average | 2.743 | 0.007 |

[1]Each value is an average of 6 individual results. Values obtained using Rheocalc V2.5 Model LV, Spindle CP40, speed 80 rpm, Shear Rate 600 1/sec, Temperature 25° C. ± 0.1

TABLE 7

Osmolality of Batches of Copaxone ® 20 mg/mL Filtered Under Controlled Room Temperature and Batches of Copaxone ® 40 mg/mL Filtered Under Reduced Temperature

| Batch No. | GA Dose | Mannitol Dose | Average Osmolality | Relative Standard Deviation (RSD) |
| --- | --- | --- | --- | --- |
| Copaxone ® 40 mg/mL No. 1 | 40 mg/ml | 40 mg/ml | 303 mosmol/Kg | 1.2 |
| Copaxone ® 40 mg/mL No. 2 | 40 mg/ml | 40 mg/ml | 300[1] mosmol/Kg | 1.7 |
| Copaxone ® 40 mg/mL No. 3 | 40 mg/ml | 40 mg/ml | 302 mosmol/Kg | 2.1 |
| Copaxone ® 20 mg/mL No. 1 | 20 mg/ml | 40 mg/ml | 268 mosmol/Kg | 2.6 |
| Copaxone ® 20 mg/mL No. 2 | 20 mg/ml | 40 mg/ml | 264 mosmol/Kg | 1.2 |
| Placebo | 0 mg/ml | 40 mg/ml | 227 mosmol/Kg | 0 |

[1]Calculated from 4 measurements.

The results show that the osmolality of batches of Copaxone® 40 mg/mL were well within the ranges of an isotonic solution.

The results also show that the batches of Copaxone® 40 mg/mL conformed to the general parenteral drug product osmolality limits of 300±30 mosmol/Kg. Further, the results indicate that batches of Copaxone® 20 mg/mL were slightly hypotonic.

What is claimed:

1. A process of preparing a pharmaceutical preparation of glatiramer acetate and mannitol in a suitable container comprising the steps of:
   (i) obtaining an aqueous pharmaceutical solution of glatiramer acetate and mannitol;
   (ii) filtering the aqueous pharmaceutical solution at a temperature of above 0° C. to 17.5° C. to produce a filtrate, wherein the filterability of the aqueous pharmaceutical solution is improved compared to the filterability of the solution at controlled room temperature; and
   (iii) filling the suitable container with the filtrate obtained after performing step (ii), so as to thereby prepare the pharmaceutical preparation of glatiramer acetate and mannitol in the suitable container.

2. The process of claim 1, wherein the filtering step (ii) comprises filtering the aqueous pharmaceutical solution through a first filter, or a first filter and a second filter.

3. The process of claim 2 further comprising the step of reducing the temperature of the second filter to a temperature of above 0° C. to 17.5° C.

4. The process of claim 2 further comprising the step of reducing the temperature of the aqueous pharmaceutical solution to a temperature of above 0° C. to 17.5° C. before passing through the second filter.

5. The process of claim 2, wherein the filtering step (ii) further comprises the step of receiving the aqueous pharmaceutical solution filtered through the first filter in a receiving vessel.

6. The process of claim 5 further comprising the step of reducing the temperature of the aqueous pharmaceutical solution to a temperature of above 0° C. to 17.5° C. after leaving the receiving vessel and before entering into the second filter.

7. The process of claim 5 further comprising the step of reducing the temperature of the aqueous pharmaceutical solution to a temperature of above 0° C. to 17.5° C. while in the receiving vessel.

8. The process of claim 2 further comprising the step of reducing the temperature of the first filter to a temperature of above 0° C. to 17.5° C.

9. The process of claim 2 further comprising the step of reducing the temperature of the aqueous pharmaceutical solution to a temperature of above 0° C. to 17.5° C. before passing through the first filter.

10. The process of claim 2, wherein the obtaining step (i) comprises compounding the aqueous pharmaceutical solution in a compounding vessel.

11. The process of claim 10 further comprising the step of reducing the temperature of the aqueous pharmaceutical solution to a temperature of above 0° C. to 17.5° C. after leaving the compounding vessel and before entering into the first filter.

12. The process of claim 10 further comprising the step of reducing the temperature of the aqueous pharmaceutical solution to a temperature of above 0° C. to 17.5° C. while in the compounding vessel.

13. The process of claim 2, wherein the aqueous pharmaceutical solution is passed through the second filter at a rate of 3-25 liters/hour; at a rate of 3-22 liters/hour; at a rate of 3-15 liters/hour; or at a rate of 3-10 liters/hour.

14. The process of claim 1, wherein the pressure during the filtering step (ii) and the pressure during the filling step (iii) is maintained below 2.0 bar.

15. The process of claim 1, wherein the temperature of the aqueous pharmaceutical solution is between 0° C. and 14° C., or the temperature of the aqueous pharmaceutical solution is reduced to a temperature between 0° C. and 14° C.

16. The process of claim 1, wherein the temperature of the aqueous pharmaceutical solution is between 0° C. and 12° C., or the temperature of the aqueous pharmaceutical solution is reduced to a temperature between 0° C. and 12° C.

17. The process of claim 1, wherein the temperature of the aqueous pharmaceutical solution is 2° C.-12° C., or the temperature of the aqueous pharmaceutical solution is reduced to 2° C.-12° C.

18. The process of claim 1, wherein the temperature of the aqueous pharmaceutical solution is 4° C.-12° C., or the temperature of the aqueous pharmaceutical solution is reduced to 4° C.-12° C.

19. The process of claim 1, wherein the filtering is performed using a sterilizing filter having a pore size of 0.2 µm or less, wherein the first, the second or both filters are a sterilizing filter having a pore size of 0.2 µm or less.

20. The process of claim 1, wherein the pharmaceutical preparation in the suitable container is an aqueous pharmaceutical solution comprising 20 mg/ml glatiramer acetate and 40 mg/ml mannitol.

21. The process of claim 1, wherein the pharmaceutical preparation in the suitable container is an aqueous pharmaceutical solution comprising 40 mg/ml glatiramer acetate and 40 mg/ml mannitol.

22. The process of claim 1, wherein the pharmaceutical preparation in the suitable container is an aqueous pharmaceutical solution having a pH in the range of 5.5-7.0.

23. The process of claim 1, wherein the pharmaceutical preparation in the suitable container is an aqueous pharmaceutical solution which is a sterilized aqueous solution which has been sterilized by filtration and without subjecting the aqueous pharmaceutical solution to heat or radiation exposure.

24. The process of claim 1, wherein the pharmaceutical preparation is a lyophilized powder of glatiramer acetate and mannitol.

25. The process of claim 1 further comprising a step of lyophilizing the filtrate after it has been filled into the suitable container so as to form a lyophilized powder of glatiramer acetate and mannitol in the suitable container.

26. The process of claim 1, wherein the suitable container is a syringe, vial, ampoule, cartridge or infusion.

27. The process of claim 26, wherein the suitable container is a syringe, wherein the syringe contains 1 ml of an aqueous pharmaceutical solution.

* * * * *